(12) United States Patent
Pfleger et al.

(10) Patent No.: US 10,370,690 B2
(45) Date of Patent: *Aug. 6, 2019

(54) MICROORGANISMS FOR PRODUCING GLYCOGEN AND METHODS OF USING SAME

(71) Applicant: WISCONSIN ALUMNI RESEARCH FOUNDATION, Madison, WI (US)

(72) Inventors: Brian F. Pfleger, Madison, WI (US); Andrew L. Markley, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/213,319

(22) Filed: Dec. 7, 2018

(65) Prior Publication Data
US 2019/0093138 A1 Mar. 28, 2019

Related U.S. Application Data

(63) Continuation of application No. 15/366,676, filed on Dec. 1, 2016.

(60) Provisional application No. 62/262,106, filed on Dec. 2, 2015.

(51) Int. Cl.
C12P 19/04 (2006.01)
C12N 1/20 (2006.01)
C12N 9/12 (2006.01)

(52) U.S. Cl.
CPC ............. *C12P 19/04* (2013.01); *C12N 1/20* (2013.01); *C12N 9/1241* (2013.01); *C12Y 207/07027* (2013.01)

(58) Field of Classification Search
None
See application file for complete search history.

(56) References Cited

U.S. PATENT DOCUMENTS

2016/0333384 A1* 11/2016 Silverman ............ A23K 20/163

OTHER PUBLICATIONS

Diaz-Troya et al., "Redox regulation of glycogen biosynthesis in the cyanobacterium Synechocystis sp. PCC 6803: Analysis of the AGP and glycogen synthases", Molecular Plant, vol. 7, No. 1, pp. 87-100, 2014 (Year: 2014).*

Aikawa et al., "Improving polyglucan production in cyanobacteria and microalgae via cultivation design and metabolic engineering", Biotechnology Journal, vol. 10, pp. 886-898, 2015 (Year: 2015).*

* cited by examiner

*Primary Examiner* — Richard C Ekstrom
(74) *Attorney, Agent, or Firm* — Daniel A. Blasiole; DeWitt LLP

(57) ABSTRACT

Recombinant microorganisms configured for increased glycogen production. The recombinant microorganisms comprise a recombinant nucleic acid configured to express or overexpress a glucose-1-phosphate adenylyltransferase. The recombinant microorganisms produce an increased amount of glycogen compared to a corresponding microorganism not comprising the recombinant nucleic acid.

20 Claims, 6 Drawing Sheets

Specification includes a Sequence Listing.

MICROORGANISMS FOR PRODUCING GLYCOGEN AND METHODS OF USING SAME

STATEMENT REGARDING FEDERALLY SPONSORED RESEARCH

This invention was made with government support under GE01215871 and EFRI1240268 awarded by the National Science Foundation. The government has certain rights in the invention.

FIELD OF THE INVENTION

The invention is directed to recombinant microorganisms configured for producing high levels of glycogen and methods of using the recombinant microorganisms for the production of glycogen or its byproducts.

BACKGROUND

Advances in microbe engineering for the production of biofuels, chemicals, and therapeutics have spurred investment in the production of a wide variety of commodities from biological sources (Zhang F, Rodriguez S, Keasling J D. 2011. *Curr. Opin. Biotechnol.* 22(6):775-83). Heterotrophic microbes comprise the vast majority of microorganisms currently utilized for product generation and require a carbohydrate source for carbon and energy that can account for a significant proportion (~60%) of input costs (Pimentel D, Patzek T W. 2008. Ethanol production: energy and economic issues related to U.S. and Brazilian sugarcane biofuels. Springer, Amsterdam, Netherlands.). Such carbohydrate feedstocks are typically derived from agricultural crops, primarily sugarcane, sugar beet, and corn, although lignocellulosic materials are under extensive investigation as alternative feedstocks (Sims R, Taylor M. 2008. From 1st to 2nd generation biofuel technologies. IEA, Paris, France). While biologically produced fuels and chemicals hold the promise of increased sustainability and reduced $CO_2$ footprints, current feedstock sources place biotechnological processes in competition with agricultural croplands and food markets. The development of biological alternatives to standard petroleum-based fuels and chemicals has therefore been criticized for its capacity to increase food cost and instabilities (Timilsina G R, Beghin J C, van der Mensbrugghe D, Mevel S. 2010. The impacts of biofuel targets on land-use change and food supply. The World Bank Development Research Group, Washington, D.C.). Indeed, in recent years, sugar prices have increased and fluctuated greatly in global food, driven in part by increased demands for biofuel production.

Photosynthetic microorganisms (cyanobacteria and algae) have been proposed as alternative sources for the creation of biofuel-like compounds or industrial feedstocks (Radakovits R, Jinkerson R E, Darzins A, Posewitz M C. 2010. *Eukaryot. Cell* 9:486-501), in part because they possess many advantages over traditional terrestrial plants with regard to targeted metabolite production. For example, the photosynthetic efficiency of cyanobacteria is up to an order of magnitude higher than that of plants (Zhu X G, Long S P, Ort D R. 2010. *Annu. Rev. Plant Biol.* 61:235-261) (Zhu X G, Long S P, Ort D R. 2008. *Curr. Opin. Biotechnol.* 19:153-159.), and cyanobacteria do not require support tissues that further reduce productive output (e.g., roots/stems). Cyanobacteria are genetically tractable, allowing for rapid engineering and the selection of desirable strains. Finally, cyanobacteria are aquatic microbes with minimal nutritional requirements and can therefore be cultivated in locations that do not compete with traditional agricultural crops. While cyanobacteria and algae share many similar features in this context, the use of algal species for biofuel feedstocks has been explored in much greater detail, partly because of their relatively high lipid content (Sheehan J, Dunahay T, Benemann J, Roessler P. 1998. Look back at the U.S. Department of Energy's aquatic species program: biodiesel from algae. Close-out report NREL/TP-580-24190. National Renewable Energy Laboratory, Golden, Colo.), although many cyanobacterial species feature relative simplicity and higher growth rates.

Glycogen that accumulates in microorganisms can serve as a valuable feedstock for the production of chemicals and biofuels. Glycogen can be converted to ethanol or other chemicals, for example, through saccharification and fermentation processes (Aikawa et al. *Energ Environ Sci* 2013, 6:1844-1849) (Choi et al. *Bioresour Technol* 2010, 101: 5330-5336) (Harun et al. *Appl Energy* 2011, 88:3464-3467) (Ho et al. *Bioresour Technol* 2013, 145:142-149) (Miranda et al. *Bioresour Technol* 2012, 104:342-348).

There is a need for microorganisms capable of producing high amounts of glycogen or other carbohydrates, particularly through photosynthetic processes.

SUMMARY OF THE INVENTION

The present invention is directed at least in part to microorganisms, such as photosynthetic microorganisms, that are capable of producing high levels of glycogen; methods of producing glycogen; and methods for selecting microorganisms that produce high levels of glycogen or other metabolic products.

The objects and advantages of the invention will appear more fully from the following detailed description of the preferred embodiment of the invention made in conjunction with the accompanying drawings.

DETAILED DESCRIPTION OF THE INVENTION

Figure 1A:
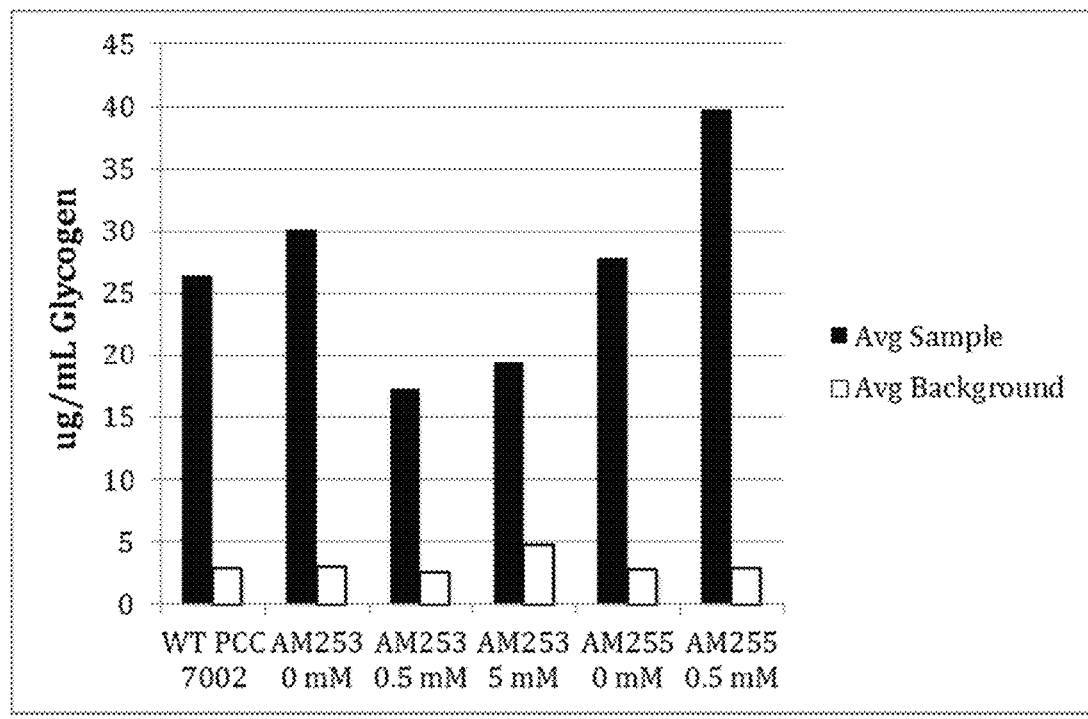
FIGS. 1A-1C show glycogen production in control strains and strains of the invention in the presence of 0, 0.5 or 5 mM isopropyl β-D-1-thiogalactopyranoside (IPTG).

The invention is directed at least in part to microorganisms capable of enhanced production of glycogen.

The microorganism of the present invention may include any microorganism capable of making glycogen. The microorganism may be eukaryotic, such as yeast, or prokaryotic, such as bacteria or archaea. Among bacteria, gram-positive, gram-negative, and ungrouped bacteria are suitable. Phototrophs, chemotrophs, heterotrophs, and autotrophs (e.g., chemoautotrophs, photoautotrophs, chemoheterotrophs, photoheterotrophs) are suitable. The phototroph may be an anoxygenic photosynthetic microorganism or an oxygenic photosynthetic mircoorganism. The oxygenic photosynthetic microorganism may be a cyanobacterium or a microalga. Suitable cyanobacteria include those from the genuses *Agmenellum*, *Anabaena*, *Aphanocapsa*, *Arthrosprira*, *Gloeocapsa*, *Haplosiphon*, *Mastigocladus*, *Nostoc*, *Oscillatoria*, *Prochlorococcus*, *Scytonema*, *Synechococcus*, and *Synechocystis*. Preferred cyanobacteria include those selected from the group consisting of *Synechococcus* spp., spp., *Synechocystis* spp., and *Nostoc* spp. Particularly suitable examples of *Synechococcus* spp. include *Synechococcus* sp. PCC 7942 and *Synechococcus* sp. PCC 7002. A particularly suitable example of *Synechocystis* spp. includes *Synechocystis* sp. PCC 6803. A benefit of photoautotrophs such as cyanobacteria is that they require only $CO_2$ as a carbon source and light for energy and are not dependent on food-based commodities or other types of biomass for which there is a growing high demand.

The microorganisms of the invention may be modified to increase expression of one or more enzymes. Modifying the microorganism to increase expression of an enzyme can be performed using any methods currently known in the art or discovered in the future. Examples include genetically modifying the microorganism and culturing the microorganism under conditions or in the presence of factors that increase expression of the enzyme. Suitable methods for genetic modification include but are not limited to placing the coding sequence under the control of a more active promoter (either inducible or constitutive), increasing gene copy number, introducing a translational enhancer (see, e.g., Olins et al. *Journal of Biological Chemistry*, 1989, 264(29): 16973-16976), and/or increasing expression of transactivators. Increasing gene copy number can be performed by introducing additional copies of the gene to the microorganism, i.e., by incorporating one or more exogenous copies of the native gene or a heterologous homolog thereof into the microbial genome, by introducing such copies to the microorganism on a plasmid or other vector, or by other means. "Exogenous" used in reference to a genetic element means the genetic element is either not present in the native organism or is not present in the native organism in the same configuration. "Heterologous" used in reference to a genetic element means that the genetic element is derived from a different species. A promoter that controls a particular coding sequence is herein described as being "operationally connected" to the coding sequence.

The microorganisms of the invention may include at least one recombinant nucleic acid configured to express or overexpress a particular enzyme. "Recombinant" as used herein with reference to a nucleic acid molecule or polypeptide is one that has a sequence that is not naturally occurring, such as a sequence that made by an artificial combination of two otherwise separated segments of sequence from the same or different organisms, or a sequence made by artificial combination of a naturally occurring sequence with a non-naturally occurring sequence. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially modified but contain the same regulatory sequences and coding regions that are found in the organism from which the nucleic acid was isolated. A recombinant cell or microorganism is one that contains a recombinant nucleic acid molecule or polypeptide. "Overexpress" as used herein means that a particular gene product is produced at a higher level in one cell, such as a recombinant cell, than in a corresponding microorganism. For example, a microorganism that includes a recombinant nucleic acid configured to overexpress an enzyme produces the enzyme at a greater amount than a microorganism that does not include the recombinant nucleic acid.

As used herein, "corresponding microorganism" refers to a microorganism of the same species having the same or substantially same genetic and proteomic composition as a microorganism of the invention, with the exception of genetic and proteomic differences resulting from the modifications described herein for the microorganisms of the invention. In some versions, the corresponding microorganism is the native microorganism. "Native" in this context refers to the natural, unmodified microorganism as it exists in nature.

Some microorganisms of the invention include at least one recombinant nucleic acid configured to express or overexpress a glucose-1-phosphate adenylyltransferase. The recombinant nucleic acid may comprise a recombinant glucose-1-phosphate adenylyltransferase gene. "Gene" refers to a nucleic acid sequence capable of producing a gene product and may include such genetic elements as a coding sequence together with any other genetic elements required for transcription and/or translation of the coding sequence. Such genetic elements may include a promoter, an enhancer, and/or a ribosome binding site (RBS), among others. The recombinant gene preferably comprises at least one sequence difference from the natural gene.

Glucose-1-phosphate adenylyltransferase include enzymes classified under EC 2.7.7.27. Glucose-1-phosphate adenylyltransferase include enzymes that catalyze the conversion of adenosine triphosphate (ATP) and α-D-glucose 1-phosphate to diphosphate and adenosine diphosphate (ADP)-glucose. In some versions, the microorganism is modified to harbor a nucleic acid encoding a glucose-1-phosphate adenylyltransferase from *Escherichia coli* or a homolog thereof. An exemplary coding sequence for a glucose-1-phosphate adenylyltransferase (glgC) from *E. coli* is represented by SEQ ID NO: 1. An exemplary amino acid sequence for a glucose-1-phosphate adenylyltransferase from *E. coli* (GlgC) is represented by SEQ ID NO:2. The native glucose-1-phosphate adenylyltransferase from *E. coli* has been shown to be activated by fructose-1,6-bisphosphate and inhibited by adenosine monophosphate (AMP) and ADP through allosteric regulation. Homologs of the *E. coli* glucose-1-phosphate adenylyltransferase include orthologs and paralogs of GlgC/glgC having glucose-1-phosphate adenylyltransferase activity. Homologs of the *E. coli* glucose-1-phosphate adenylyltransferase also include enzymes having an amino acid sequence at least about 80%, 85%, 90%, 95%, 97%, 98%, 99% or more identical to SEQ ID NO:2. Sequences having these percent identities can be obtained by aligning SEQ ID NO:2 to the sequences of *E. coli* glucose-1-phosphate adenylyltransferase orthologs and/or paralogs having glucose-1-phosphate adenylyltransferase activity to determine which positions in the enzyme are amenable to mutation (i.e., substitution, deletion, addition, etc.) and the identities of the substituted or added residues at these positions.

In preferred versions of the invention, the glucose-1-phosphate adenylyltransferase expressed by the microorganism maintains allosteric regulation by AMP and/or ADP. In particularly preferred versions of the invention, the glucose-1-phosphate adenylyltransferase expressed by the microorganism maintains full allosteric regulation by AMP and/or ADP. The maintenance of allosteric regulation with the glucose-1-phosphate adenylyltransferase is determined with respect to the wild-type glucose-1-phosphate adenylyltransferase in the type of organism from which the glucose-1-phosphate adenylyltransferase is derived, wherein "wild-type" refers to the allele that encodes the phenotype most common in the natural population. Variants or "mutants" of glucose-1-phosphate adenylyltransferase resistant to allosteric regulation by AMP and ADP are known. See, e.g., Leung P, Lee Y M, Greenberg E, Esch K, Boylan S, Preiss J. Cloning and expression of the *Escherichia coli* glgC gene from a mutant containing an ADPglucose pyrophosphorylase with altered allosteric properties. *J Bacteriol.* 1986 July; 167(1):82-8. One such variant is the *E. coli* GlgC variant having a G336D substitution (coding sequence: SEQ ID NO:3; protein sequence: SEQ ID NO:4). The G336D variant has reduced allosteric regulation with respect to the wild-type *E. coli* glgC represented by SEQ ID NO:2 and is a more active form of the enzyme. Expression of the G336D variant in cyanobacteria, however, adversely affects growth rate. Expression of glucose-1-phosphate adenylyltransferases that have a glycine at a position corresponding to position 336 of SEQ ID NO:2 (*E. coli* GlgC) are therefore preferred. In some versions, however, expression of glucose-1-phosphate adenylyltransferases that have an amino acid other than glycine at a position corresponding to position 336 of SEQ ID NO:2 (*E. coli* GlgC) are acceptable. Exemplary amino acids other than glycine include acidic amino acids, such as glutamic acid and aspartic acid, among others. Identification of the corresponding position in a given sequence can be found by aligning the sequence with SEQ ID NO:2.

The glucose-1-phosphate adenylyltransferase expressed by the microorganism preferably maintains allosteric regulation by AMP and/or ADP to an extent such that 50% inhibition of the glucose-1-phosphate adenylyltransferase occurs at an AMP or ADP concentration +/− about 10-fold, 9-fold, 8-fold, 7-fold, 6-fold, 5-fold, 4-fold, 3-fold, 2-fold, 1.5-fold, or 1.1-fold of the AMP or ADP concentration that induces 50% inhibition of the wild-type glucose-1-phosphate adenylyltransferase.

In some versions of the invention, the glucose-1-phosphate adenylyltransferase expressed by the microorganism maintains allosteric regulation by AMP, ADP, and/or fructose-1,6-bisphosphate.

Exogenous, heterologous nucleic acids encoding enzymes to be expressed in the microorganism are preferably codon-optimized for the particular microorganism in which they are introduced. Codon optimization can be performed for any nucleic acid by a number of programs, including "GENEGPS"-brand expression optimization algorithm by DNA 2.0 (Menlo Park, Calif.), "GENEOPTIMIZER"-brand gene optimization software by Life Technologies (Grand Island, N.Y.), and "OPTIMUMGENE"-brand gene design system by GenScript (Piscataway, N.J.). Other codon optimization programs or services are well known and commercially available.

In some versions of the invention, the microorganism exhibits a native glycogen synthase expression level. "Native glycogen synthase expression level" refers to the level of glycogen synthase expression in the native, unmodified microorganism. In such versions, the microorganism is not modified to overexpress the glycogen synthase, wherein overexpression is defined with respect to expression in the native microorganism. Examples of a glycogen synthase in bacteria such as *E. coli* and cyanobacteria include products of glgA genes. Examples of products of glgA genes include glgA1 (SEQ ID NO:6) and glgA2 (SEQ ID NO:8) of *Synechococcus* sp. PCC 7002, encoded by glgA1 (SEQ ID NO:5) and glgA2 (SEQ ID NO:7), respectively. Accordingly, in at least some versions of the invention in which the microorganism exhibits a native glycogen synthase expression level the microorganism contains the native glgA gene(s) and/or does not include a recombinant glgA gene configured to overexpress glgA.

In some versions of the invention, the microorganism exhibits native glycogen synthase activity. "Native glycogen synthase activity" refers to the level of glycogen synthase activity in the native, unmodified microorganism. Glycogen synthase activity in the microorganism may be determined by the method described by Leung et al. (Leung P, Lee Y M, Greenberg E, Esch K, Boylan S, Preiss J. Cloning and expression of the *Escherichia coli* glgC gene from a mutant containing an ADPglucose pyrophosphorylase with altered allosteric properties. *J Bacteriol.* 1986 July; 167(1):82-8) and Kawajuchi et al. (Kawaguchi K, Fox J, Holmes E, Boyer C, Preiss J. De novo synthesis of *Escherichia coli* glycogen is due to primer associated with glycogen synthase and activation by branching enzyme. *Arch Biochem Biophys.* 1978 October; 190(2):385-97).

In some versions of the invention, the microorganism exhibits a native 1,4-alpha-glucan-branching enzyme expression level. "Native 1,4-alpha-glucan-branching enzyme expression level expression level" refers to the level of 1,4-alpha-glucan-branching enzyme expression in the native, unmodified microorganism. In such versions, the microorganism is not modified to overexpress the 1,4-alpha-glucan-branching enzyme, wherein overexpression is defined with respect to expression in the native (non-modified) microorganism. Examples of a 1,4-alpha-glucan-branching enzyme in bacteria such as *E. coli* and cyanobacteria include products of glgB genes. An example of a product of a glgB gene includes glgB (SEQ ID NO:10) of *Synechococcus* sp. PCC 7002, which is encoded by glgB (SEQ ID NO:9). Accordingly, in at least some versions of the invention in which the microorganism exhibits a native 1,4-alpha-glucan-branching enzyme expression level the microorganism contains the native glgB gene(s) and/or does not include a recombinant glgB gene configured to overexpress glgB.

In some versions of the invention, the microorganism exhibits native 1,4-alpha-glucan-branching enzyme activity. "Native 1,4-alpha-glucan-branching enzyme activity" refers to the level of 1,4-alpha-glucan-branching enzyme activity in the native, unmodified microorganism. 1,4-Alpha-glucan-branching enzyme activity in the microorganism may be determined by the method described by Leung et al. (Leung P, Lee Y M, Greenberg E, Esch K, Boylan S, Preiss J. Cloning and expression of the *Escherichia coli* glgC gene from a mutant containing an ADPglucose pyrophosphorylase with altered allosteric properties. *J Bacteriol.* 1986 July; 167(1):82-8) and Boyer et al. (Boyer C, Preiss J. Biosynthesis of bacterial glycogen. Purification and properties of the *Escherichia coli* B alpha-1,4,-glucan: alpha-1,4-glucan 6-glycosyltansferase. *Biochemistry*. 1977 Aug. 9; 16(16): 3693-9.).

In some versions of the invention, the microorganism exhibits a native fructose-bisphosphate aldolase enzyme expression level. "Native fructose-bisphosphate aldolase enzyme expression level expression level" refers to the level of fructose-bisphosphate aldolase enzyme expression in the native, unmodified microorganism. In such versions, the microorganism is not modified to overexpress the fructose-bisphosphate aldolase enzyme, wherein overexpression is defined with respect to expression in the native (non-modified) microorganism. Examples of a fructose-bisphosphate aldolase enzyme in bacteria such as *E. coli* and cyanobacteria include products of fba genes. An example of a product of a fba gene includes fba (SEQ ID NO:12) of *Synechocystis* sp. PCC 6803, which is encoded by fba (SEQ ID NO:11). Accordingly, in at least some versions of the invention in which the microorganism exhibits a native fructose-bisphosphate aldolase enzyme expression level the microorganism contains the native fba gene(s) and/or does not include a recombinant fba gene configured to overexpress fba. In some versions of the invention, the microorganism exhibits native fructose-bisphosphate aldolase enzyme activity.

In some versions of the invention, the microorganism exhibits a native fructose 1,6-bisphosphatase enzyme expression level. "Native fructose 1,6-bisphosphatase enzyme expression level expression level" refers to the level of fructose 1,6-bisphosphatase enzyme expression in the native, unmodified microorganism. In such versions, the microorganism is not modified to overexpress the fructose 1,6-bisphosphatase enzyme, wherein overexpression is defined with respect to expression in the native (non-modified) microorganism. Examples of a fructose 1,6-bisphosphatase enzyme in bacteria such as *E. coli* and cyanobacteria include products of fbp genes. An example of a product of a fbp gene includes fbp (SEQ ID NO:14) of *Synechocystis* sp. PCC 6803, which is encoded by fbp (SEQ ID NO:11). Accordingly, in at least some versions of the invention in which the microorganism exhibits a native fructose 1,6-bisphosphatase enzyme expression level the microorganism contains the native fbp gene(s) and/or does not include a recombinant fba gene configured to overexpress fbp. In some versions of the invention, the microorganism exhibits native fructose 1,6-bisphosphatase enzyme activity.

The microorganism of the invention may comprise modifications that reduce or ablate the activity of gene products of one or more genes. Such a modification that that reduces or ablates the activity of gene products of one or more genes is referred to herein as a "functional deletion" of the gene product. "Gene product" refers to a protein or polypeptide encoded and produced by a particular gene.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations such as substitutions, partial or complete deletions, insertions, or other variations to a coding sequence or a sequence controlling the transcription or translation of a coding sequence; placing a coding sequence under the control of a less active promoter; blocking transcription of the gene with a trans-acting DNA binding protein such as a TAL effector or CRISPR guided Cas9; expressing ribozymes or antisense sequences that target the mRNA of the gene of interest; and tagging proteins for rapid proteolytic decay (Cameron D E, Collins J J. Tunable protein degradation in bacteria. *Nat Biotechnol*. 2014 December; 32(12):1276-81.), etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding microorganism. In certain versions, the genetic modifications giving rise to a functionally deleted gene product are determined with respect to the gene or coding sequence in its unaltered state as found in nature. In certain versions, the genetic modifications giving rise to a functionally deleted gene product are determined with respect to the gene or coding sequence in its form in a corresponding microorganism.

Homologs include genes or gene products (including enzymes) that are derived, naturally or artificially, from a common ancestral gene or gene product. Homology is generally inferred from sequence similarity between two or more genes or gene products. Homology between genes may be inferred from sequence similarity between the products of the genes. The precise percentage of similarity between sequences that is useful in establishing homology varies with the gene or gene product at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the coding sequences, genes, or gene products described herein include coding sequences, genes, or gene products, respectively, having at least about 30%, 35%, 40%, 45%, 50%, 55%, 60%, 65%, 70%, 75%, 80%, 85%, 90%, 95%, or 99% identity to the coding sequences, genes, or gene products, respectively, described herein. In some versions, homologs of the genes described herein include genes that have gene products at least about 30%, 35%, 40%, 45%, 50%, 55%, 60%, 65%, 70%, 75%, 80%, 85%, 90%, 95%, or 99% identical to the gene products of the genes described herein. Methods for determining sequence similarity percentages (e.g., BLASTP and BLASTN using default parameters) are described herein and are generally available. The homologous gene products should demonstrate comparable activities and, if an enzyme, participate in the same or analogous pathways. "Orthologs" are genes or coding sequences thereof in different species that evolved from a common ancestral gene by speciation. Normally, orthologs retain the same or similar function in the course of evolution. As used herein "orthologs" are included in the term "homologs." Homologs also include paralogs.

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to coding sequences, genes, or gene products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical", in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous" without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Accordingly, homologs of the genes described herein include genes with gene products at least about 80%, 85%, 90%, 95%, 97%, 98%, 99%, or more identical to the gene products of the genes described herein.

In some versions, the microorganisms of the invention produce an increased amount of glycogen compared to a corresponding microorganism not comprising the modifications described herein. For example, the microorganisms of the invention may be capable of producing at least about 1.1-fold, about 1.25-fold, about 1.5-fold, about 1.75-fold, about 2-fold, about 2.25-fold, about 2.5-fold, about 2.75-fold, about 3-fold or more glycogen than a corresponding microorganism, and/or up to about 2.5-fold, about 3-fold, about 4-fold, about 5-fold, about 10-fold, or more glycogen than a corresponding microorganism.

In some versions, the microorganisms of the invention produce glycogen at an increased rate compared to a corresponding microorganism not comprising the modifications described herein. For example, the microorganisms of the invention may be capable of producing glycogen at a rate at least about 2-fold, about 3-fold, about 4-fold, about 5-fold, about 6-fold, about 7-fold, about 8-fold, about 9-fold or more than a corresponding microorganism, and/or up to about 5-fold, about 10-fold, about 12-fold, about 15-fold or more than a corresponding microorganism.

In some versions, the microorganisms of the invention produce glycogen at a rate of at least about 50 mg/L/day, about 100 mg/L/day, about 125 mg/L/day, about 150 mg/L/day, about 175 mg/L/day, about 200 mg/L/day, or more, and/or up to about 190 mg/L/day, about 200 mg/L/day, about 225 mg/L/day, about 250 mg/L/day, about 275 mg/L/day, about 300 mg/L/day or more.

In some versions, the microorganisms of the invention are capable of producing glycogen as a mass percent of dry cell weight (DCW) in an amount of at least about 10% DCW, at least about 15% DCW, at least about 20% DCW, at least about 25% DCW, at least about 26% DCW, at least about 27% DCW, at least about 28% DCW, at least about 29% DCW, at least about 30% DCW, at least about 31% DCW, at least about 32% DCW, at least about 33% DCW, at least about 34% DCW, or at about least 35% DCW and/or up to about or at least about 31% DCW, about or at least about 32% DCW, about or at least about 33% DCW, about or at least about 34% DCW, about or at least about 35% DCW, about or at least about 36% DCW, about or at least about 37% DCW, about or at least about 38% DCW, about or at least about 39% DCW, or about or at least about 40% DCW.

In some versions, the microorganisms of the invention have a growth rate substantially the same as a corresponding microorganism when cultured under identical conditions, such that the modifications described herein do not substantially affect the growth rate. For example, the microorganisms of the invention may have a growth rate within about 40%, about 35%, about 30%, about 25%, about 20%, about 15%, about 10%, about 5%, about 3%, about 2%, or about 1% the growth rate of a corresponding microorganism when cultured under identical conditions. In some versions, the microorganisms of the invention have a growth rate of at least the growth rate of a corresponding microorganism when cultured under identical conditions.

In addition to the microorganism itself, the invention also provides methods of producing glycogen with the microorganisms of the present invention. The methods involve culturing the microorganism in conditions suitable for growth of the microorganism. Such conditions include providing suitable carbon and energy sources for the particular microorganism. Suitable carbon and energy sources for particular types of microorganisms are described elsewhere herein for exemplary microorganisms and are otherwise known in the art.

The invention also provides methods of screening for production of glycogen or other metabolic products. The screening methods generally involve culturing microorganisms under conditions that promote production of the metabolic product, then stressing the microorganisms under stringent conditions that promote consumption of the metabolic product at a high metabolic rate, and then comparing the recovery rates of the microorganisms when reintroduced to more suitable growth conditions.

An exemplary screening method includes culturing microorganisms in the presence of a carbon source and a first amount of an energy source under conditions suitable for producing the metabolic product, then culturing the microorganisms in the presence of a second amount of the energy source under conditions suitable for consuming the metabolic product, then culturing the microorganisms in the presence of the carbon source and a third amount of the energy source and determining the relative growth of the microorganisms in the presence of the carbon source and the third amount of the energy source. The second amount of the energy source is preferably less than the first amount of the energy source, and the third amount of the energy source is preferably greater than the second amount of the energy source.

The metabolic product preferably comprises a product comprising reduced carbon that serves as a form of stored energy for the microorganism and is consumable by the microorganism for survival when a sufficient external energy source is lacking. Such products may include carbohydrates, lipids, and/or proteins. Exemplary carbohydrates may include simple carbohydrates such as monosaccharides or disaccharides or complex carbohydrates such as trisaccharides, tetrasaccharides, starch, or glycogen, among others. Exemplary lipids may include fatty acids, glycerol, or glycerides, among others.

The energy source may comprise a fermentable or oxidizable form of reduced molecules, if the microorganism is a chemotroph, or light, if the microorganism is an autotroph. The reduced molecules may be organic or inorganic. Examples of reduced organic molecules include reduced carbon, such as carbohydrates, lipids, proteins, methane, and other reduced organic molecules. Reduced organic molecules can be used for chemoorganotrophs. Examples of reduced inorganic molecules include iron(II), $Mn^{2+}$, $H_2$, sulfide ($H_2S$), inorganic sulfur ($S_0$), thiosulfate ($S_2O_3^{2-}$), ammonia, and nitrite, among others. Reduced inorganic molecules can be used for chemolithotrophs.

The carbon source may comprise organic carbon, if the microorganism is a hetrotroph, or carbon dioxide, if the microorganism is an autotroph. Examples of organic carbon include carbohydrates, lipids, and proteins.

The microorganisms used in the selection method may comprise any microorganism described herein.

The conditions suitable for consuming the metabolic product preferably comprise a temperature sufficient to support metabolic activity of the microorganisms in the presence of the second amount of the energy source. Such a temperature may be at least about 27° C., at least about 30° C., at least about 35° C., at least about 37° C., at least about 40° C. or more and/or up to about 37° C., up to about 40° C., up to about 45° C. or more.

In exemplary versions of the invention, the microorganisms comprise photosynthetic microorganisms, the carbon source comprises $CO_2$, the energy source comprises light, and the metabolic product comprises glycogen. Culturing the microorganisms in the first amount of the energy source may comprise exposing the microorganisms to a direct source of light. Culturing the microorganisms in the second amount of the energy source may comprise substantially blocking the microorganisms from any direct source of light. Culturing the microorganisms in the third amount of the energy source may comprise exposing the microorganisms to a direct source of light. The photosynthetic microorganisms may comprise cyanobacteria and/or microalgae.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Strains fba (coding sequence: SEQ ID NO:11; protein sequence: SEQ ID NO:12) and fbp (coding sequence: SEQ ID NO:13; protein sequence: SEQ ID NO:14) from *Synechocystis* PCC 6803 was inserted as an operon into the cLac143 IPTG inducible cassette described in Markley et al. 2015 (Markley A L, Begemann M B, Clarke R E, Gordon G C, Pfleger B F. *ACS Synth Biol.* 2015 May 15; 4(5):595-603) with 500 base pair flanking regions targeting the acsA locus in PCC 7002, forming construct pALM173 (SEQ ID NO:15). Wild Type glgC from K12 MG1655 *E. coli* genomic DNA (coding sequence: SEQ ID NO:1; protein sequence: SEQ ID NO:2) was inserted into the cLac94 IPTG inducible cassette described in Markley et al. 2015 with 500 base-pair flanking regions targeting the glpK locus in PCC 7002, forming construct pALM210 (SEQ ID NO:16). glgC with a G336D mutation (coding sequence: SEQ ID NO:3; protein sequence: SEQ ID NO:4) was amplified from a BioBrick part BBa K118016 and inserted into an identical vector backbone as pALM210 to form pALM211 (SEQ ID NO:17).

These genetic elements were inserted into the PCC 7002 chromosome by adding 1-1.5 µg of purified plasmid DNA to 1 mL of an overnight culture of cells grown to an $OD_{730}$ of 1. The cultures were then placed at 37° C. under illumination for 16 hours. The cells were plated on 50 µM acrylic acid (acsA locus) or 100 µg/ml gentamycin (glpK locus) to select for recombinants. This yielded strains were AM184 (WT 7002 AcsA::cLac143 FbaFbp), AM241 (WT 7002 glpK::cLac94 GlgC K12 GmR) and AM253 (WT 7002 glpK::cLac94 GlgC K12 G336D GmR). Double fba-fbp/glgC strains were constructed by repeating the pALM210/pALM211 glgC transformations in the AM184 fba-fbp strain to produce AM254 (AM184 7002 glpK::cLac94 GlgC K12 GmR) and AM255 (AM184 7002 glpK::cLac94 GlgC K12 G336D GmR).

The generated strains are shown in Table 1.

TABLE 1

Strains used in the present examples.

| Strain ID | Description | Parent Strain | Construct Name(s) |
|---|---|---|---|
| AM184 | WT 7002 AcsA::cLac143 FbaFbp Fix | PCC 7002 | pALM173 |
| AM241 | WT 7002 glpK::cLac94 GlgC K12 GmR | PCC 7002 | pALM210 |
| AM253 | WT 7002 glpK::cLac94 GlgC K12 G336D GmR | PCC 7002 | pALM211 |
| AM254 | AM184 7002 glpK::cLac94 GlgC K12 GmR | PCC 7002 | pALM173 + pALM210 |
| AM255 | AM184 7002 glpK::cLac94 GlgC K12 G336D GmR | PCC 7002 | pALM173 + pALM211 |

Initial Glycogen Production Testing

Initial experiments on the produced strains were performed in Corning Costar non-treated 6-well tissue culture plates with 6 mL of MediaA+ (0.308 M NaCl, 0.02 M $MgSO_4.7H_2O$, 0.08 mM $Na_2EDTA.2H_2O$, 8.05 mM KCl, 2.52 mM $CaCl_2.2H_2O$, 11.8 mM $NaNO_3$, 0.37 mM $KH_2PO_4$, 8.26 mM TRIZMA® base (Sigma-Aldrich, St. Louis, Mo.) pH 8.2, 55.5 mM $H_3BO_3$, 0.23 mM $ZnCl_2$, 0.021 mM $MoO_3$ (85%), 0.3 µM vitamin B12 (cyanocobalamin), 0.14 mM $FeCl_3.6H_2O$, 0.22 mM $MnCl_2.4H_2O$, 0.00012 mM $CuSO_4.5H_2O$, 0.0005 mM $CoCl_2.6H_2O$) according to the UTEX Culture Collection of Algae at The University of Texas at Austin. IPTG was added at 0.5 mM and 5 mM. The cultures were grown on a shaker at 37° C. under illumination for 2 days. The induced strains with glgC G336D (AM253 and AM255) had a severe growth defect. 1.5 $OD_{730}$*mL were collected and pelleted. The pellets were washed 3× with PBS and analyzed for glycogen content using the Glycogen Assay Kit (Item No. 700480) from Cayman Chemical Company (Ann Arbor, Mich.).

To prepare samples for the glycogen assay with the Glycogen Assay Kit, 1× Glycogen Assay Buffer was prepared according to the manufacturer's instructions. 1.5 OD ml (approximately 400 mg DCW based on my standard curve) was taken from each culture in regular Media A at low $CO_2$ and washed 3× in PBS to remove Tris interference. Cell pellets were resuspended in 2 ml Diluted Assay Buffer+ 1×PMSF. Samples were frozen at −80° C. until further use. To finish the sample preparation for the glycogen assay, the remaining reagents were prepared according to the manufacturer's instructions. The frozen samples were sonicated on ice at 20% amplitude in 2-second bursts for 1 min total. The sample preparation was finished according to the manufacturer's instructions while also testing different dilution factors. The assay was then performed according to the manufacturer's instructions.

Figure 1B:
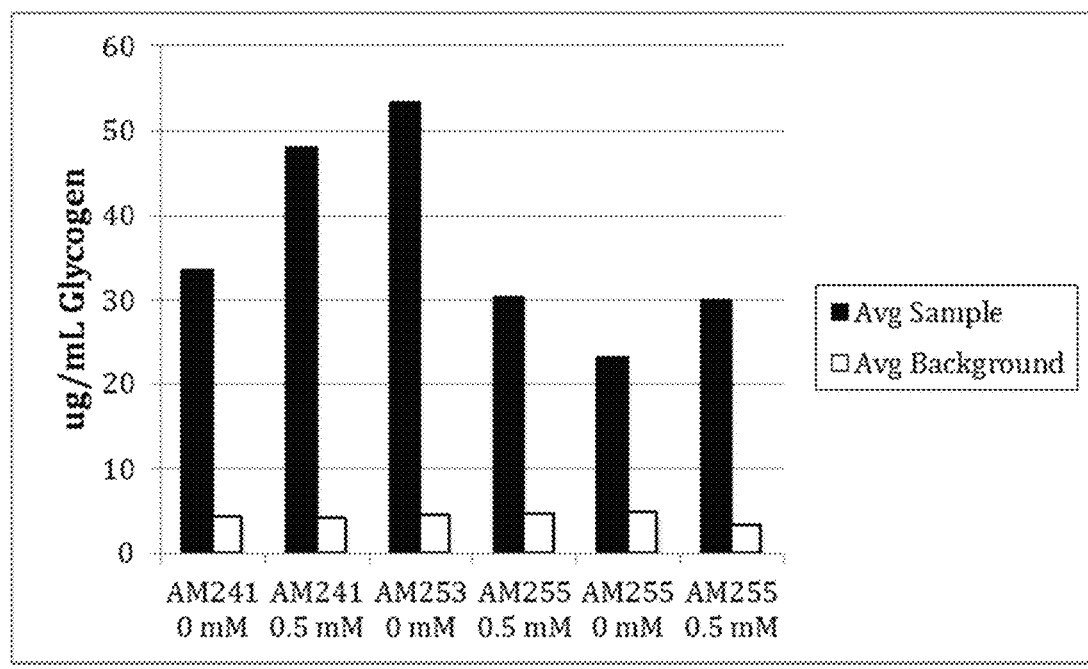
Figure 1C:
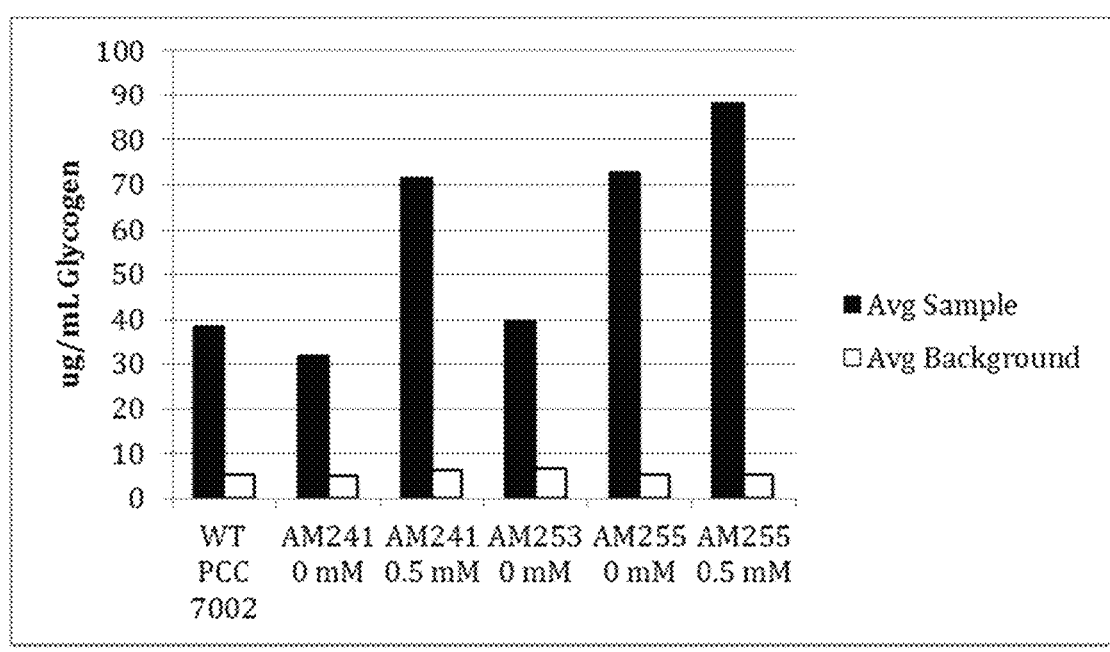

AM253 (glgC G336D) and AM255 (glgC G336D+fba-fbp) yielded inconsistent glycogen yields with these experiments, likely due to their poor growth rates. Additionally, while strains containing the glgC G336D had a high glycogen:dry cell weight ratio, the low growth rate resulted in a lower overall productivity when compared with WT glgC strains. See FIGS. 1A-1C.

Since these experiments showed that AM241 and AM254 had 2-3 fold more glycogen than WT PCC 7002 without a severe growth defect, these strains were chosen for further testing.

Glycogen Production Screen

In order to aid in the testing of the glycogen-producing strains, a screen was developed that couples glycogen content to cellular fitness. The overall scheme of this screen is to grow strains in liquid media using any desired growth condition. The cells are then normalized to the same $OD_{730}$ and serially diluted in sterile MediaA+. 7.5 µl of these dilutions are then spotted on several replicate MediaA+ agar plates. One plate is immediately placed under illumination at 37° C. while the remaining plates are placed in a dark 37° C. incubator. The plates are then periodically removed from the dark incubator and placed in the light. Cells that have a high glycogen content show higher recovery rates compared to cells with low or no glycogen content.

An alternative strategy whereby liquid cultures of high and low glycogen content strains were incubated in the dark at 37° C. for several days and periodically spotted on MediaA+ agar plates before outgrowing in the illuminated growth chamber showed no difference in cellular fitness between strains. Similarly, simply leaving the solid agar plates at room temperature instead of 37° C. also did not work as well due to the very slow loss in fitness.

Testing of Strains Using the Glycogen Production Screen

Figure 2:
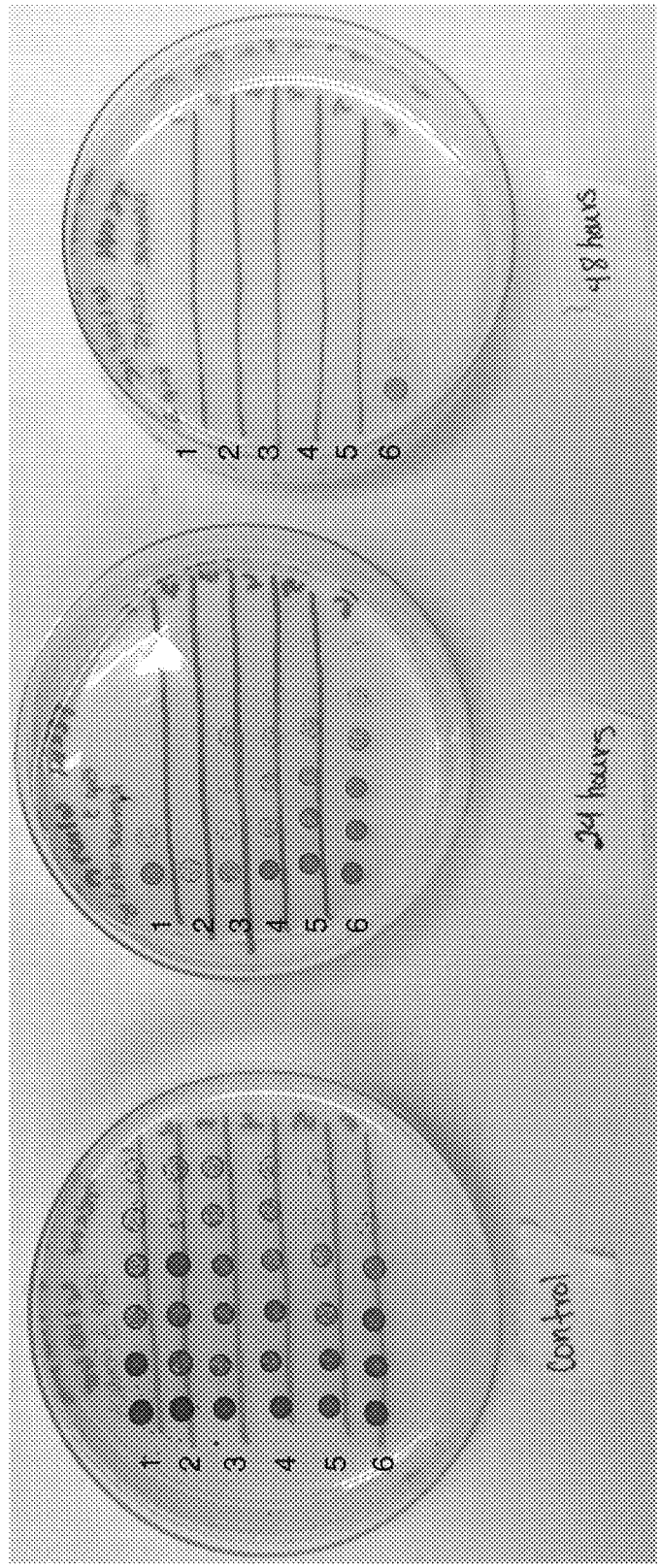
FIG. 2 shows results of a glycogen production screen of the invention with control strains and strains of the invention induced to produce glycogen in the presence of ambient $CO_2$ and 0 or 0.5 mM (IPTG).

The glycogen production screen described above was performed on WT PCC 7002, a native glgC knockout (through kanamycin resistance gene inactivation), AM241, and AM254. Each strain was inoculated at 0.05 $OD_{730}$ in 20 mL of MediaA+ and grown for 16 hours at 37° C. in the presence of ambient $CO_2$ and 0 or 0.5 mM IPTG. After 16 hours, the strains were normalized to the same $OD_{730}$, serially diluted, spotted on MediaA+ agar plates, placed in a dark 37° C. incubator for various amounts of time, and placed in the light to determine relative recovery. Results are shown in FIG. 2.

Figure 3:
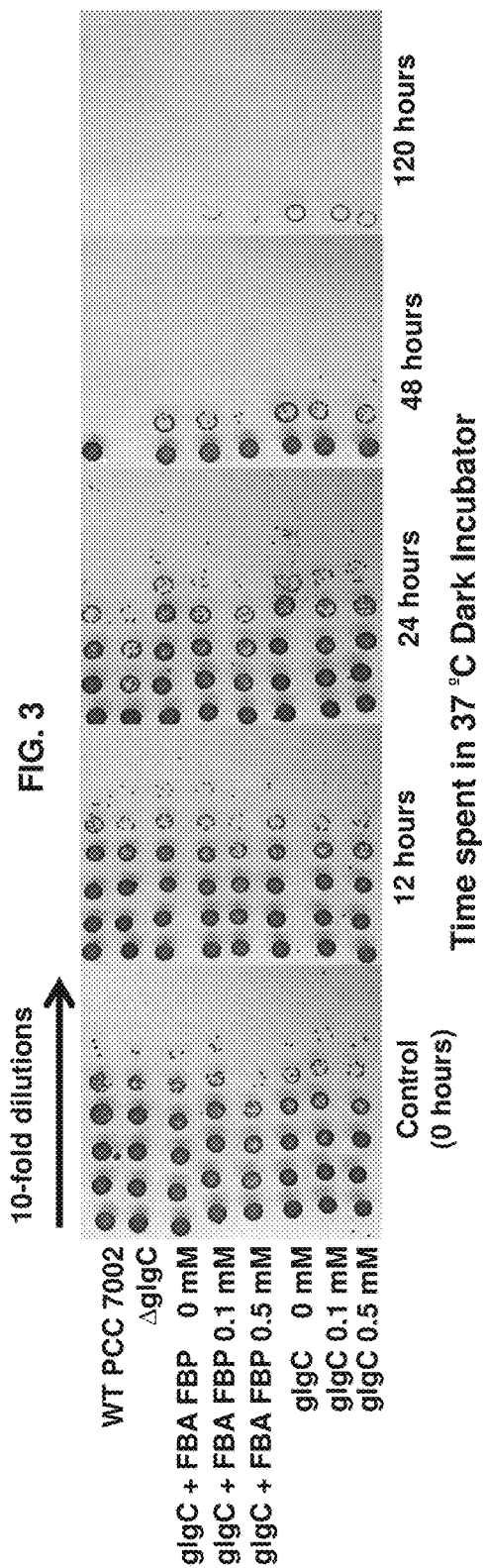
FIG. 3 shows results of a glycogen production screen of the invention with control strains and strains of the invention induced to produce glycogen in the presence of 10% $CO_2$ and 0, 0.1, or 0.5 mM (IPTG).
Figure 4:
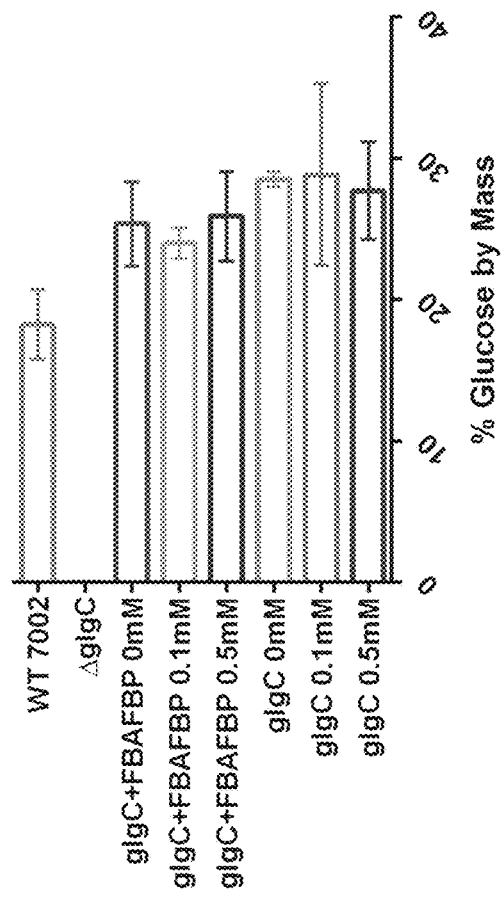
FIG. 4 shows intracellular levels of glycogen as hydrolyzed glucose from the strains analyzed in FIG. 3.

The glycogen production screen was also performed on the same strains grown in 10% $CO_2$. For this experiment, WT PCC 7002, the native glgC knockout, AM241, and AM254 were inoculated at 0.05 $OD_{730}$ in 20 mL of MediaA+ and grown for 16 hours at 37° C. with 10% $CO_2$ by volume bubbled into the tubes in the presence of 0, 0.1, or 0.5 mM IPTG. After 16 hours, the strains were normalized to the same $OD_{730}$, serially diluted, spotted on MediaA+ agar plates, placed in a dark 37° C. incubator for various amounts of time, and placed in the light to determine relative recovery. Results are shown in FIG. 3. Additionally, after the 16-hours of growth, 10 $OD_{730}$*mL of each sample were spun down and lyophilized then resuspended with 1 mL of 4% $H_2SO_4$ and placed at 121° C. for one hour to hydrolyze the glycogen to glucose. After an hour, the samples were neutralized up to a pH of >2 and then run on an HPLC with a Bio-rad Aminex HPX-87H Sugar Byproducts Column using a 5 mM $H_2SO_4$ isocratic running buffer. The glucose peaks were compared with a standard curve to determine intracellular sugar content. Results are shown in FIG. 4. The sugar content of the cells was highly correlative to the relative survival rate in the dark. Compare FIGS. 4 and 3, respectively.

The AM241 (glpK::cLac94 glgC K12 WT) strain was chosen for larger scale bioreactor studies.

Bioreactor Runs

Figure 5:
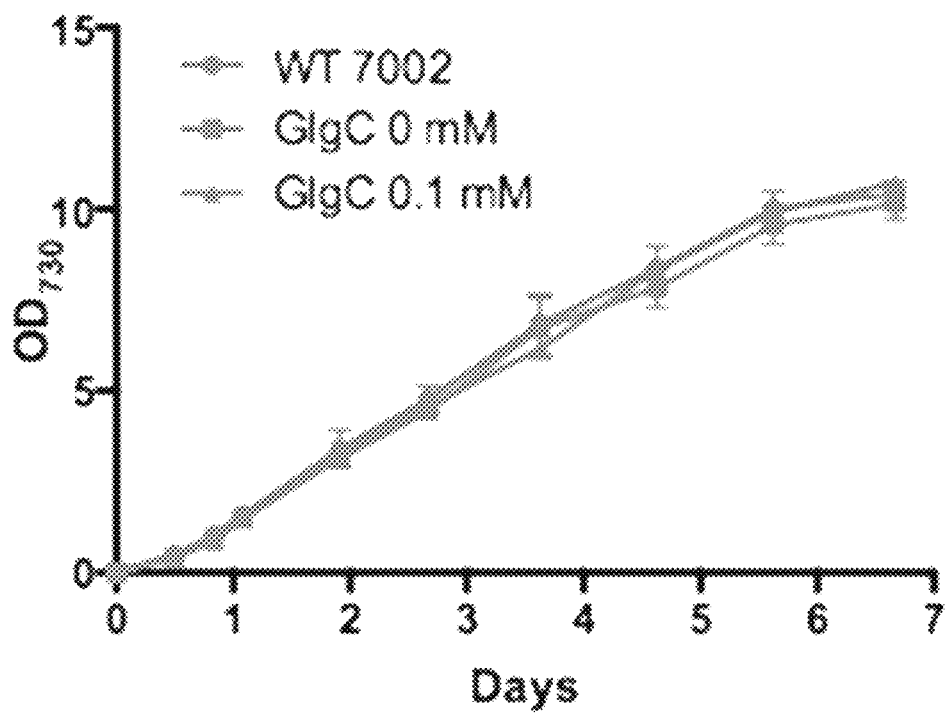
FIG. 5 shows growth rates of a control strain and a strain of the invention grown in the presence of 0 mM or 0.1 mM IPTG.
Figure 6:
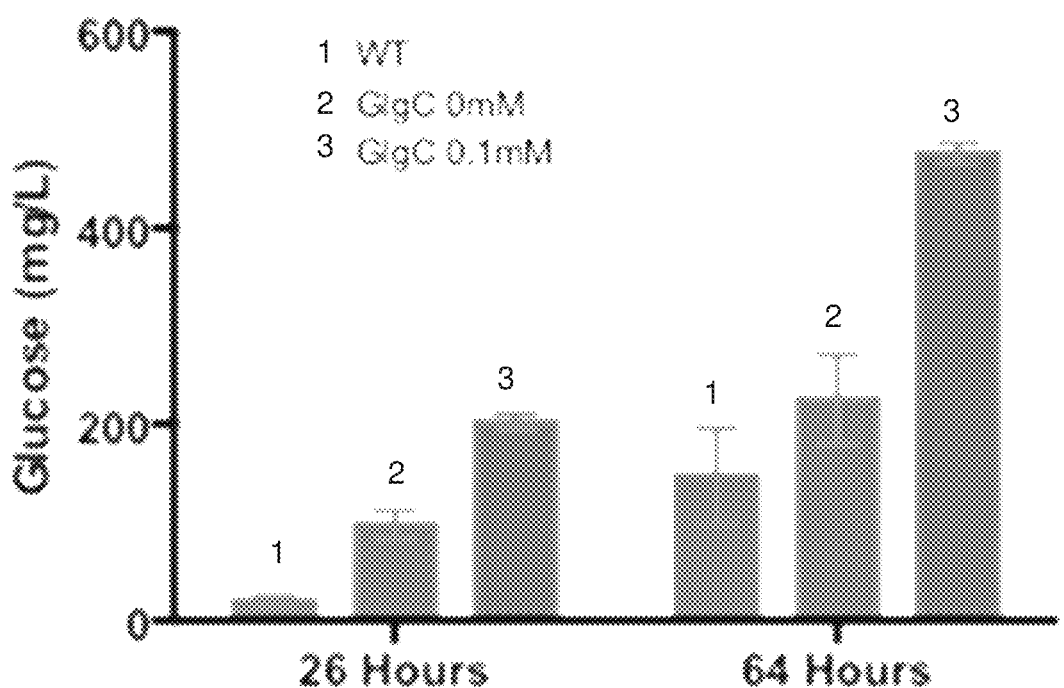
FIGS. 6, 7A, and 7B show levels of glucose hydrolyzed from glycogen from a control strain and a strain of the invention grown in the presence of 0 mM or 0.1 mM IPTG for various lengths of time.

Approximately 250 mL of WT PCC 7002 and AM241 bacteria were grown under ambient $CO_2$ conditions in the light, and then these cultures were used to inoculate 900 mL MediaA+ bioreactors in triplicate at an $OD_{730}$ of 0.01. Six total bioreactors of AM241 were inoculated, and IPTG was added to three of them to a final concentration of 0.1 mM IPTG. The bioreactors were then grown at 37° C. with 10% $CO_2$, and 60 $OD_{730}$*mL were collected periodically and analyzed for sugar content by HPLC as described above. There was no significant difference in growth rates between the WT and AM241 cultures (FIG. 5), but AM241 induced at 0.1 mM IPTG showed a 3.2 fold increase in glycogen content over WT 7002 and a titer of 476 mg/L glycogen after 64 hours (FIG. 6). Critically, this is done without having to lower the growth rate of the cyanobacteria or modify the nutrient ratios, as has been the only strategy for glycogen production in cyanobacteria.

Figure 7A:
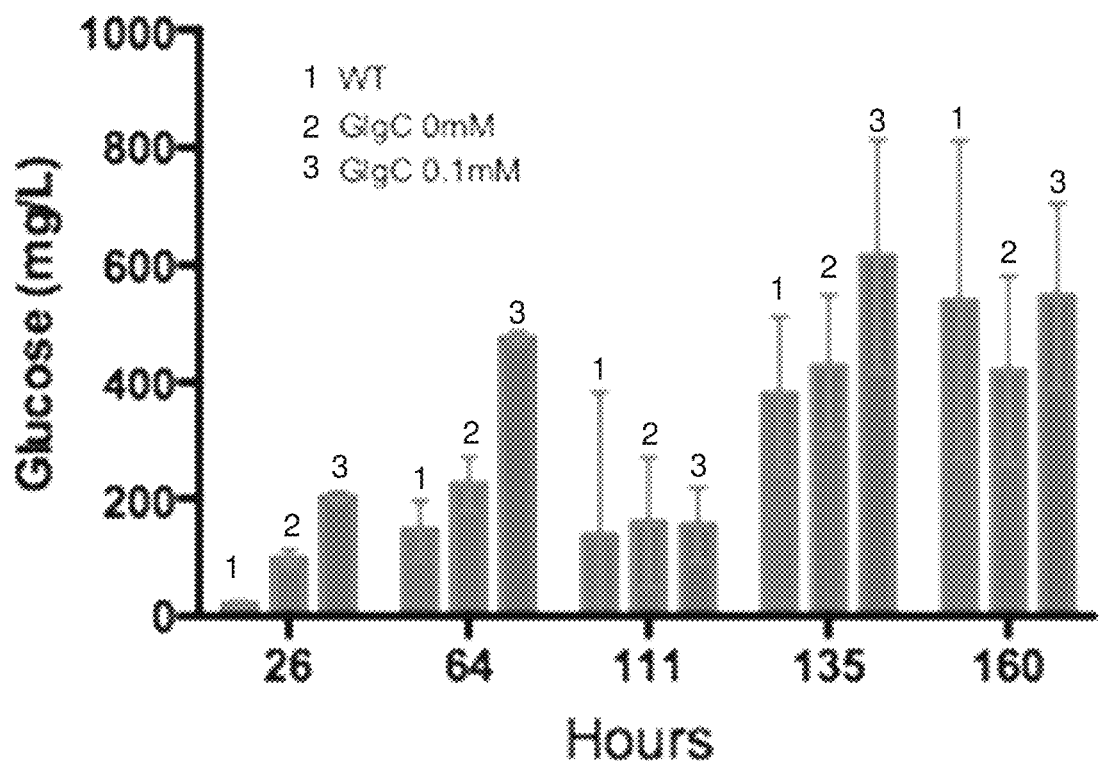
Figure 7B:
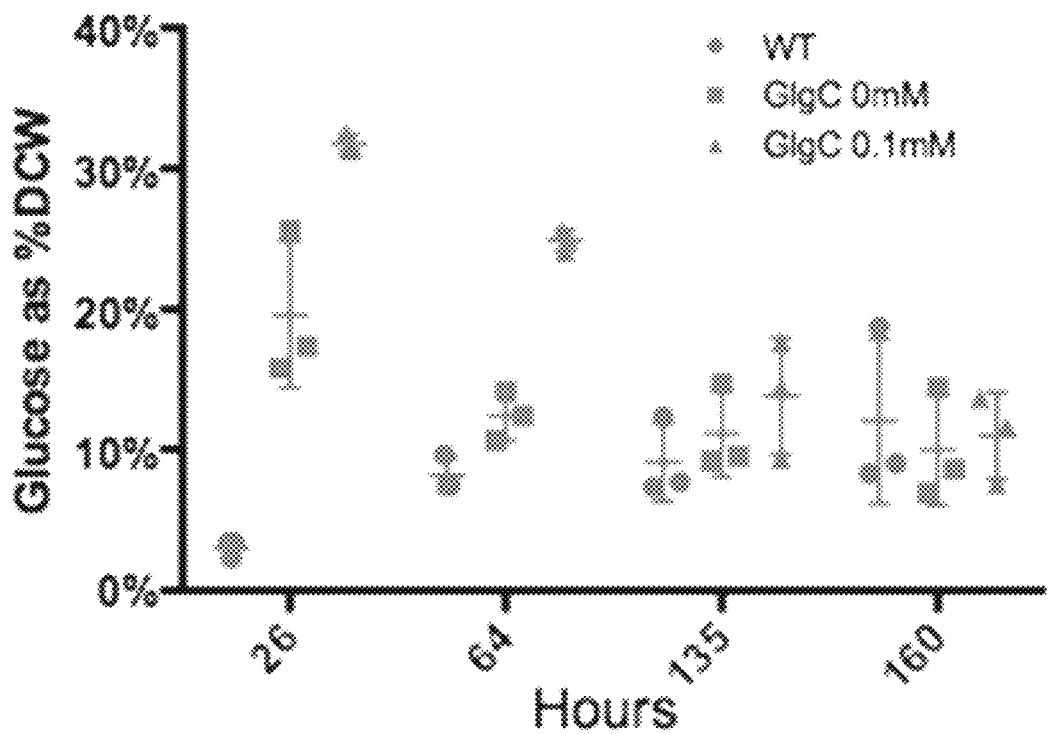

Total glycogen content did start to decrease after 64 hours. See FIGS. 7A and 7B. This decrease was likely due to IPTG degradation. It is predicted that use of a constitutive expression system will prevent such a decrease.

Additional parameters from the bioreactor experiments are shown in Table 2.

TABLE 2

Sample parameters of bioreactor runs.

| Days of Growth (Days) | Strain | Dry Cell Weight (DCW) (mg) | Sample Volume (mL) | DCW/ Sample Volume (mg/L) | HPLC Glucose Content (mg/ml) | Glucose/ Sample (mg) | Percent Glucose of DCW | Total Glucose (mg/L) | Glucose Production Rate (mg/L/day) |
|---|---|---|---|---|---|---|---|---|---|
| 1.1 | WT 7002 | 27.3 | 41.78 | 653.40 | 0.29 | 0.62 | 2.3% | 14.83 | 14 |
|  |  | 24.8 | 34.40 | 720.90 | 0.39 | 0.83 | 3.4% | 24.24 | 22 |
|  |  | 24.2 | 38.36 | 630.80 | 0.39 | 0.83 | 3.4% | 21.67 | 20 |
|  | AM241 0 mM | 23.8 | 42.02 | 566.40 | 1.75 | 3.76 | 15.8% | 89.41 | 83 |
|  |  | 16.8 | 37.41 | 449.10 | 2.00 | 4.30 | 25.6% | 115.02 | 106 |
|  |  | 22.6 | 43.35 | 521.30 | 1.82 | 3.92 | 17.4% | 90.49 | 84 |
|  | AM241 0.1 mM | 24.2 | 39.37 | 614.70 | 3.66 | 7.87 | 32.5% | 199.86 | 184 |
|  |  | 26.1 | 38.76 | 673.40 | 3.82 | 8.22 | 31.5% | 212.01 | 196 |
|  |  | 23.5 | 37.69 | 623.50 | 3.44 | 7.39 | 31.4% | 196.03 | 181 |
| 2.7 | WT 7002 | 17.2 | 12.76 | 1358.80 | 0.60 | 1.30 | 7.5% | 102.38 | 38 |
|  |  | 24.4 | 11.67 | 2090.30 | 1.08 | 2.33 | 9.6% | 199.77 | 75 |
|  |  | 25.0 | 13.57 | 1841.70 | 0.87 | 1.88 | 7.5% | 138.32 | 52 |
|  | AM241 0 mM | 24.5 | 13.89 | 1764.00 | 1.21 | 2.61 | 10.6% | 187.58 | 70 |
|  |  | 24.9 | 12.77 | 1950.50 | 1.64 | 3.52 | 14.1% | 275.91 | 103 |
|  |  | 24.1 | 14.08 | 1711.10 | 1.39 | 2.99 | 12.4% | 212.50 | 80 |
|  | AM241 0.1 mM | 25.3 | 13.10 | 1931.20 | 2.84 | 6.11 | 24.1% | 466.33 | 175 |
|  |  | 24.3 | 12.82 | 1895.40 | 2.83 | 6.09 | 25.1% | 474.95 | 178 |
|  |  | 25.8 | 13.57 | 1900.60 | 3.08 | 6.62 | 25.6% | 487.45 | 183 |
| 3.6 | WT 7002 | 25.7 | 9.12 | 2818.40 | 1.36 | 2.92 | 11.4% | 320.66 | 88 |
|  |  | 32.9 | 7.71 | 4266.00 | 2.60 | 5.60 | 17.0% | 726.09 | 200 |
|  |  | 28.8 | 9.71 | 2966.40 |  |  |  |  |  |
|  | AM241 0 mM | 23.6 | 8.04 | 2934.30 | 1.37 | 2.94 | 12.4% | 365.24 | 137 |
|  |  | 26.0 | 8.72 | 2981.30 | 2.23 | 4.79 | 18.4% | 549.06 | 206 |
|  |  | 27.3 | 10.34 | 2639.00 |  |  |  |  |  |
|  | AM241 0.1 mM | 33.5 | 9.84 | 3405.80 | 2.68 | 5.77 | 17.2% | 586.13 | 220 |
|  |  | 32.0 | 9.74 | 3285.30 | 2.72 | 5.84 | 18.3% | 599.88 | 225 |
|  |  | 64.7 | 9.68 | 6685.70 | 2.71 | 5.83 | 9.0% | 602.30 | 226 |
| 4.6 | WT 7002 | 27.2 | 7.71 | 3526.90 | 2.82 | 6.06 | 22.3% | 785.14 | 170 |
|  |  | 25.6 | 6.67 | 3840.00 | 3.86 | 8.30 | 32.4% | 1244.80 | 269 |
|  |  | 25.1 | 7.21 | 3480.50 | 2.79 | 6.00 | 23.9% | 832.15 | 180 |
|  | AM241 0 mM | 26.8 | 7.61 | 3519.70 | 3.09 | 6.65 | 24.8% | 873.35 | 189 |
|  |  | 26.0 | 7.19 | 3614.00 | 3.62 | 7.79 | 30.0% | 1082.64 | 234 |
|  |  | 26.5 | 8.26 | 3206.50 | 3.06 | 6.57 | 24.8% | 795.44 | 172 |
|  | AM241 0.1 mM | 27.9 | 7.13 | 3915.30 | 3.25 | 6.98 | 25.0% | 979.12 | 212 |
|  |  | 25.4 | 7.03 | 3615.30 | 3.41 | 7.34 | 28.9% | 1044.75 | 226 |
|  |  | 29.0 | 7.46 | 3886.00 | 3.00 | 6.44 | 22.2% | 863.37 | 187 |
| 5.6 | WT 7002 | 25.5 | 6.06 | 4207.50 | 3.57 | 7.68 | 30.1% | 1267.58 | 225 |
|  |  | 24.6 | 5.69 | 4316.70 | 3.97 | 8.54 | 34.8% | 1502.08 | 267 |
|  |  | 24.1 | 6.25 | 3856.00 | 3.57 | 7.68 | 31.9% | 1229.12 | 219 |
|  | AM241 0 mM | 24.8 | 6.22 | 3988.70 | 3.76 | 8.09 | 32.6% | 1301.43 | 231 |
|  |  | 23.0 | 5.97 | 3852.50 | 4.07 | 8.75 | 38.1% | 1466.38 | 261 |
|  |  | 24.3 | 6.67 | 3645.00 | 3.66 | 7.86 | 32.4% | 1179.50 | 210 |
|  | AM241 0.1 mM | 28.6 | 6.19 | 4623.70 | 4.62 | 9.93 | 34.7% | 1604.57 | 285 |
|  |  | 25.1 | 5.94 | 4225.20 | 4.25 | 9.15 | 36.4% | 1539.74 | 274 |
|  |  | 27.0 | 6.03 | 4477.50 | 3.84 | 8.25 | 30.6% | 1368.33 | 243 |
| 6.7 | WT 7002 | 25.6 | 5.60 | 4573.90 | 3.73 | 8.02 | 31.3% | 1432.83 | 215 |
|  |  | 25.9 | 5.70 | 4541.10 | 4.75 | 10.20 | 39.4% | 1788.97 | 268 |
|  |  | 25.6 | 6.00 | 4266.70 | 3.45 | 7.41 | 28.9% | 1234.81 | 185 |
|  | AM241 0 mM | 24.7 | 5.62 | 4396.60 | 3.23 | 6.95 | 28.1% | 1236.35 | 185 |
|  |  | 25.4 | 6.07 | 4182.50 | 4.24 | 9.11 | 35.9% | 1499.46 | 225 |
|  |  | 25.2 | 6.05 | 4166.40 | 3.61 | 7.76 | 30.8% | 1283.22 | 192 |
|  | AM241 0.1 mM | 28.5 | 5.58 | 5111.00 | 4.38 | 9.42 | 33.0% | 1689.06 | 253 |
|  |  | 26.1 | 5.47 | 4767.60 | 3.92 | 8.42 | 32.3% | 1538.89 | 231 |
|  |  | 28.8 | 5.70 | 5049.60 | 3.64 | 7.82 | 27.1% | 1370.34 | 206 |

What is claimed is:

1. A recombinant microorganism modified with respect to a native microorganism, the recombinant microorganism comprising a recombinant nucleic acid configured to express a glucose-1-phosphate adenylyltransferase, wherein the recombinant microorganism:
is a cyanobacterium;
exhibits enhanced glucose-1-phosphate adenylyltransferase activity compared to the native microorganism; and
produces an increased amount of glycogen compared to the native microorganism while having a growth rate of at least a growth rate of the native microorganism when grown photoautotrophically in the presence of light and 10% $CO_2$.

2. The recombinant microorganism of claim 1, wherein the glucose-1-phosphate adenylyltransferase is allosterically regulated by a compound selected from the group consisting of adenosine diphosphate and adenosine monophosphate.

3. The recombinant microorganism of claim 1, wherein the glucose-1-phosphate adenylyltransferase comprises a sequence at least 90% identical to SEQ ID NO:2.

4. The recombinant microorganism of claim 1, wherein the glucose-1-phosphate adenylyltransferase comprises a glycine at a position corresponding to position 336 of SEQ ID NO:2.

5. The recombinant microorganism of claim 1, wherein the nucleic acid comprises a glucose-1-phosphate adenylyltransferase coding sequence operably connected to a promoter not operably connected to the coding sequence in nature.

6. The recombinant microorganism of claim 5, wherein the promoter is an inducible promoter.

7. The recombinant microorganism of claim 5, wherein the promoter is a constitutive promoter.

8. The recombinant microorganism of claim 1, wherein the recombinant microorganism exhibits a native glycogen synthase expression level.

9. The recombinant microorganism of claim 1, wherein the recombinant microorganism exhibits native glycogen synthase activity.

10. The recombinant microorganism of claim 1, wherein the recombinant microorganism exhibits a native 1,4-alpha-glucan-branching enzyme expression level.

11. The recombinant microorganism of claim 1, wherein the recombinant microorganism exhibits native 1,4-alpha-glucan-branching enzyme activity.

12. The recombinant microorganism of claim 1, wherein the recombinant microorganism is capable of producing glycogen as a mass percent of dry cell weight (DCW) in an amount of at least about 25% DCW.

13. A method of producing glycogen comprising culturing the recombinant microorganism of claim 1.

14. The recombinant microorganism of claim 1, wherein the recombinant microorganism exhibits a native 1,4-alpha-glucan-branching enzyme expression level and native 1,4-alpha-glucan-branching enzyme activity, and wherein the recombinant microorganism is capable of producing glycogen as a mass percent of dry cell weight (DCW) in an amount of at least about 25% DCW.

15. The recombinant microorganism of claim 14, wherein the glucose-1-phosphate adenylyltransferase comprises a glycine at a position corresponding to position 336 of SEQ ID NO:2 and is allosterically regulated by a compound selected from the group consisting of adenosine diphosphate and adenosine monophosphate.

16. The recombinant microorganism of claim 14, wherein the glucose-1-phosphate adenylyltransferase comprises a sequence at least 90% identical to SEQ ID NO:2.

17. The recombinant microorganism of claim 14, wherein the nucleic acid comprises a glucose-1-phosphate adenylyltransferase coding sequence operably connected to a promoter not operably connected to the coding sequence in nature.

18. The recombinant microorganism of claim 14, wherein the recombinant microorganism exhibits a native glycogen synthase expression level.

19. The recombinant microorganism of claim 14, wherein the recombinant microorganism exhibits native glycogen synthase activity.

20. A method of producing glycogen comprising culturing the recombinant microorganism of claim 14.

* * * * *

SEQUENCE LISTING

<160> NUMBER OF SEQ ID NOS: 17

<210> SEQ ID NO 1
<211> LENGTH: 1296
<212> TYPE: DNA
<213> ORGANISM: Escherichia coli

<400> SEQUENCE: 1

```
atggttagtt tagagaagaa cgatcactta atgttggcgc gccagctgcc attgaaatct    60
gttgccctga tactggcggg aggacgtggt acccgcctga aggatttaac caataagcga   120
gcaaaaccgg ccgtacactt cggcggtaag ttccgcatta tcgactttgc gctgtctaac   180
tgcatcaact ccgggatccg tcgtatgggc gtgatcaccc agtaccagtc ccacactctg   240
gtgcagcaca ttcagcgcgg ctggtcattc ttcaatgaag aaatgaacga gtttgtcgat   300
ctgctgccag cacagcagag aatgaaaggg gaaaactggt atcgcggcac cgcagatgcg   360
gtcacccaaa acctcgacat tatccgccgt tataaagcgg aatacgtggt gatcctggcg   420
ggcgaccata tctacaagca agactactcg cgtatgctta tcgatcacgt cgaaaaaggc   480
gcacgttgca ccgttgcttg tatgccagta ccgattgaag aagcctccgc atttggcgtt   540
atggcggttg atgagaacga taaaattatc gaattcgttg aaaaacctgc taacccgccg   600
tcaatgccga acgatccgag caaatctctg gcgagtatgg gtatctacgt ctttgacgcc   660
gactatctgt atgaactgct ggaagaagac gatcgcgatg agaactccag ccacgacttt   720
ggcaaagatt tgattcccaa gatcaccgaa gccggtctgg cctatgcgca cccgttcccg   780
ctctcttgcg tacaatccga cccggatgcc gagccgtact ggcgcgatgt gggtacgctg   840
gaagcttact ggaaagcgaa cctcgatctg gcctctgtgg tgccggaact ggatatgtac   900
gatcgcaatt ggccaattcg cacctacaat gaatcattac cgccagcgaa attcgtgcag   960
gatcgctccg gtagccacgg gatgacccct aactcactgg tttccggcgg ttgtgtgatc  1020
tccggttcgg tggtggtgca gtccgttctg ttctcgcgcg ttcgcgtgaa ttcattctgc  1080
aacattgatt ccgccgtatt gttaccggaa gtatgggtag gtcgctcgtg ccgtctgcgc  1140
cgctgcgtca tcgatcgtgc ttgtgttatt ccggaaggca tggtgattgg tgaaaacgca  1200
gaggaagatg cacgtcgttt ctatcgttca gaagaaggca tcgtgctggt aacgcgcgaa  1260
atgctacgga agttagggca taaacaggag cgataa                            1296
```

<210> SEQ ID NO 2
<211> LENGTH: 431
<212> TYPE: PRT
<213> ORGANISM: Escherichia coli

<400> SEQUENCE: 2

```
Met Val Ser Leu Glu Lys Asn Asp His Leu Met Leu Ala Arg Gln Leu
1               5                   10                  15

Pro Leu Lys Ser Val Ala Leu Ile Leu Ala Gly Gly Arg Gly Thr Arg
            20                  25                  30

Leu Lys Asp Leu Thr Asn Lys Arg Ala Lys Pro Ala Val His Phe Gly
        35                  40                  45

Gly Lys Phe Arg Ile Ile Asp Phe Ala Leu Ser Asn Cys Ile Asn Ser
    50                  55                  60

Gly Ile Arg Arg Met Gly Val Ile Thr Gln Tyr Gln Ser His Thr Leu
65                  70                  75                  80

Val Gln His Ile Gln Arg Gly Trp Ser Phe Phe Asn Glu Glu Met Asn
                85                  90                  95
```

Glu Phe Val Asp Leu Leu Pro Ala Gln Gln Arg Met Lys Gly Glu Asn
                100                 105                 110

Trp Tyr Arg Gly Thr Ala Asp Ala Val Thr Gln Asn Leu Asp Ile Ile
            115                 120                 125

Arg Arg Tyr Lys Ala Glu Tyr Val Val Ile Leu Ala Gly Asp His Ile
        130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
                180                 185                 190

Val Glu Lys Pro Ala Asn Pro Pro Ser Met Pro Asn Asp Pro Ser Lys
            195                 200                 205

Ser Leu Ala Ser Met Gly Ile Tyr Val Phe Asp Ala Asp Tyr Leu Tyr
        210                 215                 220

Glu Leu Leu Glu Glu Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
                260                 265                 270

Tyr Trp Arg Asp Val Gly Thr Leu Glu Ala Tyr Trp Lys Ala Asn Leu
            275                 280                 285

Asp Leu Ala Ser Val Val Pro Glu Leu Asp Met Tyr Asp Arg Asn Trp
        290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Gly
                325                 330                 335

Gly Cys Val Ile Ser Gly Ser Val Val Val Gln Ser Val Leu Phe Ser
                340                 345                 350

Arg Val Arg Val Asn Ser Phe Cys Asn Ile Asp Ser Ala Val Leu Leu
            355                 360                 365

Pro Glu Val Trp Val Gly Arg Ser Cys Arg Leu Arg Arg Cys Val Ile
        370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Gly Ile Val Leu
                405                 410                 415

Val Thr Arg Glu Met Leu Arg Lys Leu Gly His Lys Gln Glu Arg
                420                 425                 430

<210> SEQ ID NO 3
<211> LENGTH: 1296
<212> TYPE: DNA
<213> ORGANISM: Escherichia coli

<400> SEQUENCE: 3
atggttagtt tagagaagaa cgatcactta atgttggcgc gccagctgcc attgaaatct    60
gttgccctga tactggcggg aggacgtggt acccgcctga aggatttaac caataagcga   120
gcaaaaccgg ccgtacactt cggcggtaag ttccgcatta tcgactttgc gctgtctaac   180
tgcatcaact ccgggatccg tcgtatgggc gtgatcaccc agtaccagtc ccacactctg   240

```
gtgcagcaca ttcagcgcgg ctggtcattc ttcaatgaag aaatgaacga gtttgtcgat      300
ctgctgccag cacagcagag aatgaaaggg gaaaactggt atcgcggcac cgcagatgcg      360
gtcacccaaa acctcgacat tatccgccgt tataaagcgg aatacgtggt gatcctggcg      420
ggcgaccata tctacaagca agactactcg cgtatgctta tcgatcacgt cgaaaaaggc      480
gcacgttgca ccgttgcttg tatgccagta ccgattgaag aagcctccgc atttggcgtt      540
atggcggttg atgagaacga taaaattatc gaatttgttg aaaaacctgc taacccgccg      600
tcaatgccga acgatccgag caaatctctg gcgagtatgg gtatctacgt ctttgacgcc      660
gactatctgt atgaactgct ggaagaagac gatcgcgatg agaactccag ccacgacttt      720
ggcaaagatt tgattcccaa gatcaccgaa gccggtctgg cctatgcgca cccgttcccg      780
ctctcttgcg tacaatccga cccggatgcc gagccgtact ggcgcgatgt gggtacgctg      840
gaagcttact ggaaagcgaa cctcgatctg gcctctgtgg tgccggaact ggatatgtac      900
gatcgcaatt ggccaattcg cacctacaat gaatcattac cgccagcgaa attcgtgcag      960
gatcgctccg gtagccacgg gatgacccct aactcactgg tttccgacgg ttgtgtgatc     1020
tccggttcgg tggtggtgca gtccgttctg ttctcgcgcg ttcgcgtgaa ctcattctgc     1080
aacattgatt ccgccgtatt gttaccggaa gtatgggtag gtcgctcgtg ccgtctgcgc     1140
cgctgcgtca tcgatcgtgc ttgtgttatt ccggaaggca tggtgattgg tgaaaacgca     1200
gaggaagatg cacgtcgttt ctatcgttca gaagaaggca tcgtgctggt aacgcgcgaa     1260
atgctacgga agttagggca taaacaggag cgataa                              1296
```

<210> SEQ ID NO 4
<211> LENGTH: 431
<212> TYPE: PRT
<213> ORGANISM: Escherichia coli

<400> SEQUENCE: 4

```
Met Val Ser Leu Glu Lys Asn Asp His Leu Met Leu Ala Arg Gln Leu
  1               5                  10                  15

Pro Leu Lys Ser Val Ala Leu Ile Leu Ala Gly Gly Arg Gly Thr Arg
             20                  25                  30

Leu Lys Asp Leu Thr Asn Lys Arg Ala Lys Pro Ala Val His Phe Gly
         35                  40                  45

Gly Lys Phe Arg Ile Ile Asp Phe Ala Leu Ser Asn Cys Ile Asn Ser
     50                  55                  60

Gly Ile Arg Arg Met Gly Val Ile Thr Gln Tyr Gln Ser His Thr Leu
 65                  70                  75                  80

Val Gln His Ile Gln Arg Gly Trp Ser Phe Phe Asn Glu Glu Met Asn
                 85                  90                  95

Glu Phe Val Asp Leu Leu Pro Ala Gln Gln Arg Met Lys Gly Glu Asn
            100                 105                 110

Trp Tyr Arg Gly Thr Ala Asp Ala Val Thr Gln Asn Leu Asp Ile Ile
        115                 120                 125

Arg Arg Tyr Lys Ala Glu Tyr Val Val Ile Leu Ala Gly Asp His Ile
    130                 135                 140

Tyr Lys Gln Asp Tyr Ser Arg Met Leu Ile Asp His Val Glu Lys Gly
145                 150                 155                 160

Ala Arg Cys Thr Val Ala Cys Met Pro Val Pro Ile Glu Glu Ala Ser
                165                 170                 175

Ala Phe Gly Val Met Ala Val Asp Glu Asn Asp Lys Ile Ile Glu Phe
```

```
                    180                 185                 190
Val Glu Lys Pro Ala Asn Pro Pro Ser Met Pro Asn Asp Pro Ser Lys
                195                 200                 205

Ser Leu Ala Ser Met Gly Ile Tyr Val Phe Asp Ala Asp Tyr Leu Tyr
            210                 215                 220

Glu Leu Leu Glu Glu Asp Arg Asp Glu Asn Ser Ser His Asp Phe
225                 230                 235                 240

Gly Lys Asp Leu Ile Pro Lys Ile Thr Glu Ala Gly Leu Ala Tyr Ala
                245                 250                 255

His Pro Phe Pro Leu Ser Cys Val Gln Ser Asp Pro Asp Ala Glu Pro
            260                 265                 270

Tyr Trp Arg Asp Val Gly Thr Leu Glu Ala Tyr Trp Lys Ala Asn Leu
        275                 280                 285

Asp Leu Ala Ser Val Val Pro Glu Leu Asp Met Tyr Asp Arg Asn Trp
    290                 295                 300

Pro Ile Arg Thr Tyr Asn Glu Ser Leu Pro Pro Ala Lys Phe Val Gln
305                 310                 315                 320

Asp Arg Ser Gly Ser His Gly Met Thr Leu Asn Ser Leu Val Ser Asp
                325                 330                 335

Gly Cys Val Ile Ser Gly Ser Val Val Gln Ser Val Leu Phe Ser
            340                 345                 350

Arg Val Arg Val Asn Ser Phe Cys Asn Ile Asp Ser Ala Val Leu Leu
        355                 360                 365

Pro Glu Val Trp Val Gly Arg Ser Cys Arg Leu Arg Arg Cys Val Ile
    370                 375                 380

Asp Arg Ala Cys Val Ile Pro Glu Gly Met Val Ile Gly Glu Asn Ala
385                 390                 395                 400

Glu Glu Asp Ala Arg Arg Phe Tyr Arg Ser Glu Glu Gly Ile Val Leu
                405                 410                 415

Val Thr Arg Glu Met Leu Arg Lys Leu Gly His Lys Gln Glu Arg
            420                 425                 430

<210> SEQ ID NO 5
<211> LENGTH: 1437
<212> TYPE: DNA
<213> ORGANISM: Synechococcus PCC7002

<400> SEQUENCE: 5
atgcgtattt tgtttgtttc tgccgaggct gctcccatcg ctaaagctgg aggcatggga       60
gatgtggtgg atcactgcc taaagtttta cggcagttag acatgacgc gagaattttc       120 ttaccctatt acggctttct caacgacaaa ctcgacatcc ctgcagaacc cgtttggtgg      180
ggcagtgcga tgttcaatac ttttgccgtt tatgaaactg tgttgcccaa caccgatgtc      240
ccccttttat c tgtttggcca tcccgccttt gatggacggc atatttatgg tgggcaggat     300
gaattttggc gctttacctt ttttgccaat ggggccgctg aatttatgtg aaccactgg      360 aaaccccaga tcgcccactg tcacgactgg cacacgggca tgattccggt atggatgcac      420
caatcgccgg atatcagtac ggtgtttacg atccacaact tagcctacca agggccttgg      480 cggggttttcc tggagcgcaa tacttggtgt ccctggtata tggatggtga taacgtgatg      540
gcttcggcgc tgatgtttgc cgatcaggtg aacaccgtat ctcccaccta tgcccaacaa      600
atccaaacca aagtctatgg tgaaaaatta gagggtttgt tgtcttggat cagtggcaaa      660
agtcgcggca tcgtgaatgg tattgacgta gaactttata atccttctaa cgatcaagcc      720
```

-continued

```
ctggtgaagc aatttctac gactaatctt gaggatcggg ccgccaacaa agtgattatc     780
caagaagaaa cggggctaga ggtcaactcc aaggctttt tgatggcgat ggtcacccgc     840
ttagtggaac aaaagggcat tgatctgctg ctaaatatcc tggagcagtt tatggcatac     900
actgacgccc agctcattat cctcggcact ggcgatcgcc actacgaaac ccaactctgg     960
cagactgcct accgctttaa ggggcggatg tccgtgcaac tgctctataa tgatgccctc    1020
tcccgccgga tttacgctgg atccgatgtc ttttgatgc cgtcacgctt tgagccctgt    1080
ggcattagtc aaatgatggc gatgcgctac ggttctgtac cgattgtgcg gcgcaccggg    1140
ggtttggtgg atacggtctc tttccatgat ccgattcacc aaaccgggac aggctttagt    1200
tttgaccgct acgaaccgct ggatatgtac acctgcatgg tgcgggcttg ggaaagtttc    1260
cgctacaaaa aagactgggc tgaactacaa agacgaggca tgagccatga ctttagttgg    1320
tacaaatctg ccggggaata tctcaagatg taccgccaaa gcattaaaga agctccggaa    1380
ttaacgaccg atgaagccga aaaaatcacc tatttagtga aaaacacgc catttaa       1437
```

```
<210> SEQ ID NO 6
<211> LENGTH: 478
<212> TYPE: PRT
<213> ORGANISM: Synechococcus PCC7002

<400> SEQUENCE: 6
```

| | | | | | | | | | | | | | | | |
|---|---|---|---|---|---|---|---|---|---|---|---|---|---|---|---|
| Met | Arg | Ile | Leu | Phe | Val | Ser | Ala | Glu | Ala | Ala | Pro | Ile | Ala | Lys | Ala |
| 1 | | | | 5 | | | | | 10 | | | | | 15 | |
| Gly | Gly | Met | Gly | Asp | Val | Val | Gly | Ser | Leu | Pro | Lys | Val | Leu | Arg | Gln |
| | | | 20 | | | | | 25 | | | | | 30 | | |
| Leu | Gly | His | Asp | Ala | Arg | Ile | Phe | Leu | Pro | Tyr | Tyr | Gly | Phe | Leu | Asn |
| | | | | 35 | | | | | 40 | | | | 45 | | |
| Asp | Lys | Leu | Asp | Ile | Pro | Ala | Glu | Pro | Val | Trp | Trp | Gly | Ser | Ala | Met |
| | | | 50 | | | | | 55 | | | | | 60 | | |
| Phe | Asn | Thr | Phe | Ala | Val | Tyr | Glu | Thr | Val | Leu | Pro | Asn | Thr | Asp | Val |
| 65 | | | | | 70 | | | | | 75 | | | | | 80 |
| Pro | Leu | Tyr | Leu | Phe | Gly | His | Pro | Ala | Phe | Asp | Gly | Arg | His | Ile | Tyr |
| | | | | 85 | | | | | 90 | | | | | 95 | |
| Gly | Gly | Gln | Asp | Glu | Phe | Trp | Arg | Phe | Thr | Phe | Phe | Ala | Asn | Gly | Ala |
| | | | 100 | | | | | 105 | | | | | 110 | | |
| Ala | Glu | Phe | Met | Trp | Asn | His | Trp | Lys | Pro | Gln | Ile | Ala | His | Cys | His |
| | | | | 115 | | | | | 120 | | | | 125 | | |
| Asp | Trp | His | Thr | Gly | Met | Ile | Pro | Val | Trp | Met | His | Gln | Ser | Pro | Asp |
| | | | 130 | | | | | 135 | | | | | 140 | | |
| Ile | Ser | Thr | Val | Phe | Thr | Ile | His | Asn | Leu | Ala | Tyr | Gln | Gly | Pro | Trp |
| 145 | | | | | 150 | | | | | 155 | | | | | 160 |
| Arg | Gly | Phe | Leu | Glu | Arg | Asn | Thr | Trp | Cys | Pro | Trp | Tyr | Met | Asp | Gly |
| | | | | 165 | | | | | 170 | | | | | 175 | |
| Asp | Asn | Val | Met | Ala | Ser | Ala | Leu | Met | Phe | Ala | Asp | Gln | Val | Asn | Thr |
| | | | 180 | | | | | 185 | | | | | 190 | | |
| Val | Ser | Pro | Thr | Tyr | Ala | Gln | Gln | Ile | Gln | Thr | Lys | Val | Tyr | Gly | Glu |
| | | | | 195 | | | | | 200 | | | | 205 | | |
| Lys | Leu | Glu | Gly | Leu | Leu | Ser | Trp | Ile | Ser | Gly | Lys | Ser | Arg | Gly | Ile |
| | | | 210 | | | | | 215 | | | | | 220 | | |
| Val | Asn | Gly | Ile | Asp | Val | Glu | Leu | Tyr | Asn | Pro | Ser | Asn | Asp | Gln | Ala |
| 225 | | | | | 230 | | | | | 235 | | | | | 240 |
| Leu | Val | Lys | Gln | Phe | Ser | Thr | Thr | Asn | Leu | Glu | Asp | Arg | Ala | Ala | Asn |
| | | | | 245 | | | | | 250 | | | | | 255 | |

```
Lys Val Ile Ile Gln Glu Glu Thr Gly Leu Glu Val Asn Ser Lys Ala
                260                 265                 270

Phe Leu Met Ala Met Val Thr Arg Leu Val Glu Gln Lys Gly Ile Asp
            275                 280                 285

Leu Leu Leu Asn Ile Leu Glu Gln Phe Met Ala Tyr Thr Asp Ala Gln
        290                 295                 300

Leu Ile Ile Leu Gly Thr Gly Asp Arg His Tyr Glu Thr Gln Leu Trp
305                 310                 315                 320

Gln Thr Ala Tyr Arg Phe Lys Gly Arg Met Ser Val Gln Leu Leu Tyr
                325                 330                 335

Asn Asp Ala Leu Ser Arg Arg Ile Tyr Ala Gly Ser Asp Val Phe Leu
            340                 345                 350

Met Pro Ser Arg Phe Glu Pro Cys Gly Ile Ser Gln Met Met Ala Met
        355                 360                 365

Arg Tyr Gly Ser Val Pro Ile Val Arg Arg Thr Gly Gly Leu Val Asp
    370                 375                 380

Thr Val Ser Phe His Asp Pro Ile His Gln Thr Gly Thr Gly Phe Ser
385                 390                 395                 400

Phe Asp Arg Tyr Glu Pro Leu Asp Met Tyr Thr Cys Met Val Arg Ala
                405                 410                 415

Trp Glu Ser Phe Arg Tyr Lys Lys Asp Trp Ala Glu Leu Gln Arg Arg
            420                 425                 430

Gly Met Ser His Asp Phe Ser Trp Tyr Lys Ser Ala Gly Glu Tyr Leu
        435                 440                 445

Lys Met Tyr Arg Gln Ser Ile Lys Glu Ala Pro Glu Leu Thr Thr Asp
    450                 455                 460

Glu Ala Glu Lys Ile Thr Tyr Leu Val Lys Lys His Ala Ile
465                 470                 475

<210> SEQ ID NO 7
<211> LENGTH: 1473
<212> TYPE: DNA
<213> ORGANISM: Synechococcus PCC7002

<400> SEQUENCE: 7
atgtacatcg tccagattgc ttcggaatgc gcccccgtcg cgaaggtagg tggacttgga      60
gatgtggttt acggactcag tcgcgagctt agtctgcgcg tcattgtgt cgaaatcatt     120 ttgcccaaat atgattgtct ccgttatgac cacatttggg ggatgcacga agcctatcgg     180
gatctttggg taccctggtt tggcggtgcg atccactgca ccgttttcta tggctgggtc     240
catggccaac aatgtttctt tatcgaaccc cactccggtg ataactttt cagtcggggc     300 ttttttttatg gagccttaga cgaccacatg cgctttgcct tctttagcaa ggcggccctc     360 gaattttac aaaaatccaa caaacgcccc gatattatcc actgccatga ctggcaaacc     420
ggtctcgttc cggtgatgct ctttgaaatg tacaagtggc atggcctgtg aatcagcgg     480 gtgtgctaca ccatccacaa ctttaaacat cagggtatcg cggcgctga cgtactgtgg     540 gcgacgggtc tcaataacga gggctactat ttccactacg atcgcctccg ggataacttt     600
aatccctttg ccttaaattg catgaaaggg ggcattgtct atgccaatgc ggtgacgacc     660
gtttctcccc accacgcctg ggaagcccac tacaccgata ttggttgtgg cctaagccat     720
accctccatc tccaccaaga caagttcaag ggaattctca acggcatcga ctacagcact     780
tggaacccag aagtagacca caatatcgag ctgcaataca gttgggatag cctcgaaaat     840
```

-continued

```
aaggcgaaaa acaaaaaagc cctacgcgat cgcctattac ttgaagacaa tgaccgaccg    900
atcatcgcct acattggccg tctcgatgac caaaaaggcg ttcatctcgt tcaccatgcc    960
atgtactacg ccttgaatcg gggagcccaa tttgtcctcc ttggttccgc caccgaaggc   1020
tcgatcaact cttggttctg gcatgaaaaa ttccacctca acgacaaccc caactgtcac   1080
atcgagctgg gcttcaacgc cgaactgtcc cacatgatct atgccggggc tgatatgctt   1140
gtcgtcccca gtaactacga accctgcggc ctgacccaac tcatcgccct gaagtatggt   1200
gtggtgccca ttgtccgtgg tgtcggtggc ctcgtgagta ccgtgtttga ccgggatcat   1260
gatgataaac atccccccga agaacgaaat ggttatgtct tttaccaaac ggataaccac   1320
gccctcgaat ccgccatgga acgggccatt ggtttataca ccgtgtaccc agaggagttc   1380
cggaagctgc aaatccaggg gatgaaatat gactactctt ggcataaccc cggcaatgaa   1440
tatattgatc tctatgagtt tatccgcgcc taa                                1473
```

<210> SEQ ID NO 8
<211> LENGTH: 490
<212> TYPE: PRT
<213> ORGANISM: Synechococcus PCC7002

<400> SEQUENCE: 8

Met Tyr Ile Val Gln Ile Ala Ser Glu Cys Ala Pro Val Ala Lys Val
1               5                   10                  15

Gly Gly Leu Gly Asp Val Val Tyr Gly Leu Ser Arg Glu Leu Ser Leu
            20                  25                  30

Arg Gly His Cys Val Glu Ile Ile Leu Pro Lys Tyr Asp Cys Leu Arg
        35                  40                  45

Tyr Asp His Ile Trp Gly Met His Glu Ala Tyr Arg Asp Leu Trp Val
    50                  55                  60

Pro Trp Phe Gly Gly Ala Ile His Cys Thr Val Phe Tyr Gly Trp Val
65                  70                  75                  80

His Gly Gln Gln Cys Phe Phe Ile Glu Pro His Ser Gly Asp Asn Phe
                85                  90                  95

Phe Ser Arg Gly Phe Phe Tyr Gly Ala Leu Asp Asp His Met Arg Phe
            100                 105                 110

Ala Phe Phe Ser Lys Ala Ala Leu Glu Phe Leu Gln Lys Ser Asn Lys
        115                 120                 125

Arg Pro Asp Ile Ile His Cys His Asp Trp Gln Thr Gly Leu Val Pro
    130                 135                 140

Val Met Leu Phe Glu Met Tyr Lys Trp His Gly Leu Trp Asn Gln Arg
145                 150                 155                 160

Val Cys Tyr Thr Ile His Asn Phe Lys His Gln Gly Ile Ala Gly Ala
                165                 170                 175

Asp Val Leu Trp Ala Thr Gly Leu Asn Asn Glu Gly Tyr Tyr Phe His
            180                 185                 190

Tyr Asp Arg Leu Arg Asp Asn Phe Asn Pro Phe Ala Leu Asn Cys Met
        195                 200                 205

Lys Gly Gly Ile Val Tyr Ala Asn Ala Val Thr Thr Val Ser Pro His
    210                 215                 220

His Ala Trp Glu Ala His Tyr Thr Asp Ile Gly Cys Gly Leu Ser His
225                 230                 235                 240

Thr Leu His Leu His Gln Asp Lys Phe Lys Gly Ile Leu Asn Gly Ile
                245                 250                 255

Asp Tyr Ser Thr Trp Asn Pro Glu Val Asp His Asn Ile Glu Leu Gln

```
            260                 265                 270
Tyr Ser Trp Asp Ser Leu Glu Asn Lys Ala Lys Asn Lys Lys Ala Leu
            275                 280                 285

Arg Asp Arg Leu Leu Leu Glu Asp Asn Asp Arg Pro Ile Ile Ala Tyr
            290                 295                 300

Ile Gly Arg Leu Asp Asp Gln Lys Gly Val His Leu Val His His Ala
305                 310                 315                 320

Met Tyr Tyr Ala Leu Asn Arg Gly Ala Gln Phe Val Leu Leu Gly Ser
                325                 330                 335

Ala Thr Glu Gly Ser Ile Asn Ser Trp Phe Trp His Glu Lys Phe His
            340                 345                 350

Leu Asn Asp Asn Pro Asn Cys His Ile Glu Leu Gly Phe Asn Ala Glu
            355                 360                 365

Leu Ser His Met Ile Tyr Ala Gly Ala Asp Met Leu Val Val Pro Ser
            370                 375                 380

Asn Tyr Glu Pro Cys Gly Leu Thr Gln Leu Ile Ala Leu Lys Tyr Gly
385                 390                 395                 400

Val Val Pro Ile Val Arg Gly Val Gly Gly Leu Val Ser Thr Val Phe
                405                 410                 415

Asp Arg Asp His Asp Asp Lys His Pro Pro Glu Arg Asn Gly Tyr
            420                 425                 430

Val Phe Tyr Gln Thr Asp Asn His Ala Leu Glu Ser Ala Met Glu Arg
            435                 440                 445

Ala Ile Gly Leu Tyr Thr Val Tyr Pro Glu Glu Phe Arg Lys Leu Gln
450                 455                 460

Ile Gln Gly Met Lys Tyr Asp Tyr Ser Trp His Asn Pro Gly Asn Glu
465                 470                 475                 480

Tyr Ile Asp Leu Tyr Glu Phe Ile Arg Ala
                485                 490

<210> SEQ ID NO 9
<211> LENGTH: 2334
<212> TYPE: DNA
<213> ORGANISM: Synechococcus PCC7002

<400> SEQUENCE: 9
atgcctactc tcctcactcc agaccagatc aaccaaattg tttctaacca ccatgacaac      60
ccccatgctg tcttgggttg tcatcccacc aacgacgatc ccaatccgaa aacctggtca     120
attcgcgctt atttaccttc tgctagccaa gcttgggtga ttgatacccc ttcccaaacg     180
gaacacccga tgacaacggt gcatcatccc cacttttttg aatgcacccct ccagagtgaa    240 acaacaccga atatcaact gaagctccaa gaaggcgatc gccaacacat catcaacgat      300
ccctatgcct ttgccgaagc cccccacatt agcgatctcg atctccacct ctttgccgaa     360
gggaatcacc accgcatcta acaaaactg ggggcacacc tcgtcgaagt cgatggcatc     420
aaaggcgttt actttgccgt tgggcgcccc aatgcccgca acgtctccat cctgggcgac     480
tttaacaact gggatggtcg caaacaccaa atgcgccgtt taaacgttgg tatctgggga     540
attttcattc ctgacctcgg ccccaacacc aaatacaaat acgaaatcaa aaaccaacac     600
ggccacatct acgaaaaatc agaccctac ggctttctcc gggaagtgcg ccccgacact     660
gcctccatcg ttgctgacct cgaccagtac caatggcagg atcacgattg ctagaacaa     720 cgtgccaaac aagaccccct caaaaatcct gtttccatct acgaactaca cctcggctcc     780
tggctccatg gttccgccac cgaaaaaatg caactccttt ccggtgaagt cgatcccatt     840
```

```
cccgtgggcg atcaaaaacc cggtgcccgc ttcctgagct attacgaact ggttgataag     900
ctcatcccct acgttaagga catgggctac acccacatcg agctactgcc tgtcgctgaa     960
catcccttg acggttcctg gggctaccaa gtgaccggct actattcccc cacttcccgc    1020
tttggcaatc ccgaagacct gatgtatttc atcgatcaat gccacgccaa tggtatcggg    1080
gtgatcgttg actgggttcc tggccatttc cctaaggatg cccatggtct cgcttacttc    1140
gatggcaccc atctctatga acacgccgat ccccgcaaag gtgagcacaa aggctggggc    1200
accctgatct ttaactacaa tcgcaatgag gttcgcaact tcctcattgc caatgcccta    1260
ttctggtttg ataaatatca catcgatggc attcgggtcg atgcagtggc atcaatgctc    1320
tacctcgact acgaccggga agatggcgag tggcttccca atgactacgg cggcaacgaa    1380
cacctcgaag ccgtagaatt tctccgccaa accaacaatc tcatcttcaa gtactatcca    1440
gggattatct ccgttgccga agagtccacg gcttggccca tggtttctcg tcccacttac    1500
ctcggtggcc tcggcttcaa cctcaagtgg aatatgggct ggatgcacga caatctcaaa    1560
tacttcagca tggatccctg gttccggcag caccaccaaa acagcattac cttcagtatg    1620
tggtatcatc acagcgagaa ctacatgttg gccctttccc acgatgaagt cgtccatggt    1680
aagagctcga ttattggcaa aatgccgggg gatgaatggc agaaatttgc caatgtgcgg    1740
gctttattcg cctatatgtt tacccatcct ggtaaaaaga ccatgtttat gagcatggaa    1800
tttggccaat ggaatgagtg gaatgtttgg agtgacttga gttgggattt actgcaacat    1860
gaaccccacg ccaaactcaa aggtttcttc ggggcattaa atagtctcta taaacaggaa    1920
ccggcccttt acgaacggga ttttgaagag gaaggattcc aatggattga ctgttctgac    1980
aatcaaaata gtgttctttc ctttattcga cgggcaaaag atcccaatga ttttttagtt    2040
gtggtctgca attttacgcc gcaaccccat agccattatc gaattggcat tccagaagag    2100
ggctactatc aagaaatttt gaatagtgat gccgaaacct tggggggag taatctactc    2160
aacttcggcg gcgtttggac tgaagattgg cgcttccata atcttcccta ttccattgat    2220
ctgtgtttgc cgcccctcgg cgtggttgtc ctaaaaattg atcgagaaaa acagccgca    2280
atgcttgctc aaaaacaggc cgataaagcc aaggctctat ccggcgaaat ataa         2334
```

<210> SEQ ID NO 10
<211> LENGTH: 777
<212> TYPE: PRT
<213> ORGANISM: Synechococcus PCC7002

<400> SEQUENCE: 10

```
Met Pro Thr Leu Leu Thr Pro Asp Gln Ile Asn Gln Ile Val Ser Asn
1               5                  10                  15

His His Asp Asn Pro His Ala Val Leu Gly Cys His Pro Thr Asn Asp
                20                  25                  30

Asp Pro Asn Pro Lys Thr Trp Ser Ile Arg Ala Tyr Leu Pro Ser Ala
            35                  40                  45

Ser Gln Ala Trp Val Ile Asp Thr Pro Ser Gln Thr Glu His Pro Met
        50                  55                  60

Thr Thr Val His His Pro His Phe Phe Glu Cys Thr Leu Gln Ser Glu
65                  70                  75                  80

Thr Thr Pro Lys Tyr Gln Leu Lys Leu Gln Glu Gly Asp Arg Gln His
                85                  90                  95

Ile Ile Asn Asp Pro Tyr Ala Phe Ala Glu Ala Pro His Ile Ser Asp
            100                 105                 110
```

```
Leu Asp Leu His Leu Phe Ala Glu Gly Asn His His Arg Ile Tyr Asn
        115                 120                 125

Lys Leu Gly Ala His Leu Val Glu Val Asp Gly Ile Lys Gly Val Tyr
    130                 135                 140

Phe Ala Val Trp Ala Pro Asn Ala Arg Asn Val Ser Ile Leu Gly Asp
145                 150                 155                 160

Phe Asn Asn Trp Asp Gly Arg Lys His Gln Met Arg Arg Leu Asn Val
                165                 170                 175

Gly Ile Trp Gly Ile Phe Ile Pro Asp Leu Gly Pro Asn Thr Lys Tyr
            180                 185                 190

Lys Tyr Glu Ile Lys Asn Gln His Gly His Ile Tyr Glu Lys Ser Asp
        195                 200                 205

Pro Tyr Gly Phe Leu Arg Glu Val Arg Pro Asp Thr Ala Ser Ile Val
    210                 215                 220

Ala Asp Leu Asp Gln Tyr Gln Trp Gln Asp His Asp Trp Leu Glu Gln
225                 230                 235                 240

Arg Ala Lys Gln Asp Pro Leu Lys Asn Pro Val Ser Ile Tyr Glu Leu
                245                 250                 255

His Leu Gly Ser Trp Leu His Gly Ser Ala Thr Glu Lys Met Gln Leu
            260                 265                 270

Leu Ser Gly Glu Val Asp Pro Ile Pro Val Gly Asp Gln Lys Pro Gly
        275                 280                 285

Ala Arg Phe Leu Ser Tyr Tyr Glu Leu Val Asp Lys Leu Ile Pro Tyr
    290                 295                 300

Val Lys Asp Met Gly Tyr Thr His Ile Glu Leu Leu Pro Val Ala Glu
305                 310                 315                 320

His Pro Phe Asp Gly Ser Trp Gly Tyr Gln Val Thr Gly Tyr Tyr Ser
                325                 330                 335

Pro Thr Ser Arg Phe Gly Asn Pro Glu Asp Leu Met Tyr Phe Ile Asp
            340                 345                 350

Gln Cys His Ala Asn Gly Ile Gly Val Ile Val Asp Trp Val Pro Gly
        355                 360                 365

His Phe Pro Lys Asp Ala His Gly Leu Ala Tyr Phe Asp Gly Thr His
    370                 375                 380

Leu Tyr Glu His Ala Asp Pro Arg Lys Gly Glu His Lys Gly Trp Gly
385                 390                 395                 400

Thr Leu Ile Phe Asn Tyr Asn Arg Asn Glu Val Arg Asn Phe Leu Ile
                405                 410                 415

Ala Asn Ala Leu Phe Trp Phe Asp Lys Tyr His Ile Asp Gly Ile Arg
            420                 425                 430

Val Asp Ala Val Ala Ser Met Leu Tyr Leu Asp Tyr Asp Arg Glu Asp
        435                 440                 445

Gly Glu Trp Leu Pro Asn Asp Tyr Gly Gly Asn Glu His Leu Glu Ala
    450                 455                 460

Val Glu Phe Leu Arg Gln Thr Asn Asn Leu Ile Phe Lys Tyr Tyr Pro
465                 470                 475                 480

Gly Ile Ile Ser Val Ala Glu Glu Ser Thr Ala Trp Pro Met Val Ser
                485                 490                 495

Arg Pro Thr Tyr Leu Gly Gly Leu Gly Phe Asn Leu Lys Trp Asn Met
            500                 505                 510

Gly Trp Met His Asp Asn Leu Lys Tyr Phe Ser Met Asp Pro Trp Phe
        515                 520                 525
```

```
Arg Gln His His Gln Asn Ser Ile Thr Phe Ser Met Trp Tyr His His
            530                 535                 540
Ser Glu Asn Tyr Met Leu Ala Leu Ser His Asp Glu Val Val His Gly
545                 550                 555                 560
Lys Ser Ser Ile Ile Gly Lys Met Pro Gly Asp Glu Trp Gln Lys Phe
                565                 570                 575
Ala Asn Val Arg Ala Leu Phe Ala Tyr Met Phe Thr His Pro Gly Lys
            580                 585                 590
Lys Thr Met Phe Met Ser Met Glu Phe Gly Gln Trp Asn Glu Trp Asn
            595                 600                 605
Val Trp Ser Asp Leu Ser Trp Asp Leu Leu Gln His Glu Pro His Ala
610                 615                 620
Lys Leu Lys Gly Phe Phe Gly Ala Leu Asn Ser Leu Tyr Lys Gln Glu
625                 630                 635                 640
Pro Ala Leu Tyr Glu Arg Asp Phe Glu Glu Gly Phe Gln Trp Ile
                645                 650                 655
Asp Cys Ser Asp Asn Gln Asn Ser Val Leu Ser Phe Ile Arg Arg Ala
            660                 665                 670
Lys Asp Pro Asn Asp Phe Leu Val Val Cys Asn Phe Thr Pro Gln
            675                 680                 685
Pro His Ser His Tyr Arg Ile Gly Ile Pro Glu Glu Gly Tyr Tyr Gln
            690                 695                 700
Glu Ile Leu Asn Ser Asp Ala Glu Thr Phe Gly Gly Ser Asn Leu Leu
705                 710                 715                 720
Asn Phe Gly Gly Val Trp Thr Glu Asp Trp Arg Phe His Asn Leu Pro
                725                 730                 735
Tyr Ser Ile Asp Leu Cys Leu Pro Pro Leu Gly Val Val Val Leu Lys
            740                 745                 750
Ile Asp Arg Glu Lys Thr Ala Ala Met Leu Ala Gln Lys Gln Ala Asp
            755                 760                 765
Lys Ala Lys Ala Leu Ser Gly Glu Ile
            770                 775

<210> SEQ ID NO 11
<211> LENGTH: 1080
<212> TYPE: DNA
<213> ORGANISM: Synechocystis PCC6803

<400> SEQUENCE: 11
atggctcttg taccaatgag actgctgtta gaccatgcgg cggaaaatgg ttatggcatt      60
cccgctttca acgtcaacaa catggagcag atcatttcga tcatgcaggc cgctgatgaa     120
accgacagcc ctgtaatttt gcaagcttcc cgtggtgccc ggagctacgc tggggaaaat     180
ttcctgcgcc atttagtttt ggggcggtc gaaacctatc ctcacattcc cattgccatg     240
caccaagacc acggcaatag ccccgccact tgctattccg ccatccgcaa cggtttcacc     300
agtgtgatga tggacggttc cttggaagct gacgccaaga cccccgctag ctttgagtac     360
aacgttaatg taaccgctga agtagttaaa gtagcccact ccgttggggc agtgtagaa     420 ggggaattgg gttgcttagg ttccttggaa actggtcaag gggaagctga agacggccac     480
ggttttgaag ggaagttaga ccactcccaa ctgttgaccg atcccgaaga agcagtggaa     540
ttcgtcaaca aaacccaggt ggatgccctc gctgtggcga tcggtaccag ccatggtgcc     600
tacaaattta cccgcaaacc caccggtgaa gttttggcca tcagccgcat tgaagaaatt     660
caccgcctgc tgcccaacac ccacttggta atgcacggtt cttcctccgt tccccaggaa     720
```

```
tggatcgaca tgatcaacga attcggtggt gctatccccg aaacctatgg tgtgcccgtg    780
gaagaaattc aaaaaggcat caagagtggt gtacgtaaag taaacatcga caccgataat    840
cgcttagcca tcaccgccgc tttccgggaa gccgctgcta agatcccaa gaactttgat     900 ccccgtcact tcctcaagcc ttctatcaaa tatatgaagc aggtttgtgc cgatcgctat    960
caacagttct ggactgctgg caatgcctct aaaatcaagc aattgacctt ggatgactac   1020
gccgctaaat atgccaaagg tgaattaacc gccacctccc gcacctccgt tgctgtgtag   1080
```

<210> SEQ ID NO 12
<211> LENGTH: 359
<212> TYPE: PRT
<213> ORGANISM: Synechocystis PCC6803

<400> SEQUENCE: 12

```
Met Ala Leu Val Pro Met Arg Leu Leu Asp His Ala Ala Glu Asn
1               5                   10                  15

Gly Tyr Gly Ile Pro Ala Phe Asn Val Asn Met Glu Gln Ile Ile
            20                  25                  30

Ser Ile Met Gln Ala Ala Asp Glu Thr Asp Ser Pro Val Ile Leu Gln
            35                  40                  45

Ala Ser Arg Gly Ala Arg Ser Tyr Ala Gly Glu Asn Phe Leu Arg His
        50                  55                  60

Leu Val Leu Gly Ala Val Glu Thr Tyr Pro His Ile Pro Ile Ala Met
65                  70                  75                  80

His Gln Asp His Gly Asn Ser Pro Ala Thr Cys Tyr Ser Ala Ile Arg
                85                  90                  95

Asn Gly Phe Thr Ser Val Met Met Asp Gly Ser Leu Glu Ala Asp Ala
            100                 105                 110

Lys Thr Pro Ala Ser Phe Glu Tyr Asn Val Asn Val Thr Ala Glu Val
        115                 120                 125

Val Lys Val Ala His Ser Val Gly Ala Ser Val Glu Gly Glu Leu Gly
    130                 135                 140

Cys Leu Gly Ser Leu Glu Thr Gly Gln Gly Glu Ala Glu Asp Gly His
145                 150                 155                 160

Gly Phe Glu Gly Lys Leu Asp His Ser Gln Leu Leu Thr Asp Pro Glu
                165                 170                 175

Glu Ala Val Glu Phe Val Asn Lys Thr Gln Val Asp Ala Leu Ala Val
            180                 185                 190

Ala Ile Gly Thr Ser His Gly Ala Tyr Lys Phe Thr Arg Lys Pro Thr
        195                 200                 205

Gly Glu Val Leu Ala Ile Ser Arg Ile Glu Glu Ile His Arg Leu Leu
    210                 215                 220

Pro Asn Thr His Leu Val Met His Gly Ser Ser Ser Val Pro Gln Glu
225                 230                 235                 240

Trp Ile Asp Met Ile Asn Glu Phe Gly Gly Ala Ile Pro Glu Thr Tyr
                245                 250                 255

Gly Val Pro Val Glu Glu Ile Gln Lys Gly Ile Lys Ser Gly Val Arg
            260                 265                 270

Lys Val Asn Ile Asp Thr Asp Asn Arg Leu Ala Ile Thr Ala Ala Phe
        275                 280                 285

Arg Glu Ala Ala Ala Lys Asp Pro Lys Asn Phe Asp Pro Arg His Phe
    290                 295                 300

Leu Lys Pro Ser Ile Lys Tyr Met Lys Gln Val Cys Ala Asp Arg Tyr
```

```
                305                 310                 315                 320
Gln Gln Phe Trp Thr Ala Gly Asn Ala Ser Lys Ile Lys Gln Leu Thr
                    325                 330                 335

Leu Asp Asp Tyr Ala Ala Lys Tyr Ala Lys Gly Glu Leu Thr Ala Thr
                340                 345                 350

Ser Arg Thr Ser Val Ala Val
            355

<210> SEQ ID NO 13
<211> LENGTH: 1044
<212> TYPE: DNA
<213> ORGANISM: Synechocystis PCC6803

<400> SEQUENCE: 13
atgaccgtta gtgagattca tattcctaac tctttactag accgggattg caccacccct      60
tcacgccacg tactccaaca actgaatagc tttggggccg atgcccagga tttgagtgcc     120
atcatgaacc gcattgccct agcgggaaaa ctgattgccc gtcgcctgag tcgagctggg     180
ttaatggccg atgtgttggg cttcactggg gaaaccaacg tccaggggga atcggtgaaa     240
aaaatggacg tatttgccaa tgatgttttt atttctgtct ttaagcaaag tggcttggtt     300
tgtcgtctgg cttcggagga gatggaaaaa ccctactata ttcctgaaaa ttgccccatt     360
ggtcgctata ctttgctgta cgaccccatt gatggttcct ccaacgtgga cattaacctc     420
aacgtgggtt ccattttgc cattcggcaa caggaagggg acgatctaga cggcagtgcg      480
tcagatttat tggctaacgg agacaagcaa attgctgctg ttatatcct ctacggcccc      540 tccaccatcc tggtttattc cctcggctcc ggagtgcata gctttatcct cgatcccagt     600
ttgggggaat ttatttttagc ccaggaaaat atccgcattc caaccacgg ccccattac      660 agcaccaatg aaggtaactt ttggcaatgg gatgaagccc tgagggatta cacccgttac     720
gtccatcgcc acgaaggtta cactgcccgt tatagcggtg ctctggtggg ggatattcac     780
cggattttga tgcaagggg agtgtttctt tatcctggta cggaaaaaaa tcccgacggc     840
aaattgcgtt tgctctatga aactgcgccg ctggcctttt tggtggaaca ggctggggga     900
agggctagtg acggccaaaa acgtttactg gacttaattc cttctaaatt acatcagcgt     960
acccccgcca ttattggcag cgcagaagat gtgaaattgg tggaatcttt catcagcgac    1020
cacaaacaac ggcagggtaa ttag                                           1044

<210> SEQ ID NO 14
<211> LENGTH: 347
<212> TYPE: PRT
<213> ORGANISM: Synechocystis PCC6803

<400> SEQUENCE: 14

Met Thr Val Ser Glu Ile His Ile Pro Asn Ser Leu Leu Asp Arg Asp
1               5                   10                  15

Cys Thr Thr Leu Ser Arg His Val Leu Gln Gln Leu Asn Ser Phe Gly
            20                  25                  30

Ala Asp Ala Gln Asp Leu Ser Ala Ile Met Asn Arg Ile Ala Leu Ala
        35                  40                  45

Gly Lys Leu Ile Ala Arg Arg Leu Ser Arg Ala Gly Leu Met Ala Asp
    50                  55                  60

Val Leu Gly Phe Thr Gly Glu Thr Asn Val Gln Gly Glu Ser Val Lys
65                  70                  75                  80

Lys Met Asp Val Phe Ala Asn Asp Val Phe Ile Ser Val Phe Lys Gln
```

```
                 85                  90                  95
    Ser Gly Leu Val Cys Arg Leu Ala Ser Glu Glu Met Glu Lys Pro Tyr
                100                 105                 110

Tyr Ile Pro Glu Asn Cys Pro Ile Gly Arg Tyr Thr Leu Leu Tyr Asp
                115                 120                 125

Pro Ile Asp Gly Ser Ser Asn Val Asp Ile Asn Leu Asn Val Gly Ser
                130                 135                 140

Ile Phe Ala Ile Arg Gln Gln Glu Gly Asp Asp Leu Asp Gly Ser Ala
    145                 150                 155                 160

Ser Asp Leu Leu Ala Asn Gly Asp Lys Gln Ile Ala Ala Gly Tyr Ile
                165                 170                 175

Leu Tyr Gly Pro Ser Thr Ile Leu Val Tyr Ser Leu Gly Ser Gly Val
                180                 185                 190

His Ser Phe Ile Leu Asp Pro Ser Leu Gly Glu Phe Ile Leu Ala Gln
                195                 200                 205

Glu Asn Ile Arg Ile Pro Asn His Gly Pro Ile Tyr Ser Thr Asn Glu
                210                 215                 220

Gly Asn Phe Trp Gln Trp Asp Glu Ala Leu Arg Asp Tyr Thr Arg Tyr
    225                 230                 235                 240

Val His Arg His Glu Gly Tyr Thr Ala Arg Tyr Ser Gly Ala Leu Val
                245                 250                 255

Gly Asp Ile His Arg Ile Leu Met Gln Gly Gly Val Phe Leu Tyr Pro
                260                 265                 270

Gly Thr Glu Lys Asn Pro Asp Gly Lys Leu Arg Leu Leu Tyr Glu Thr
                275                 280                 285

Ala Pro Leu Ala Phe Leu Val Glu Gln Ala Gly Gly Arg Ala Ser Asp
                290                 295                 300

Gly Gln Lys Arg Leu Leu Asp Leu Ile Pro Ser Lys Leu His Gln Arg
    305                 310                 315                 320

Thr Pro Ala Ile Ile Gly Ser Ala Glu Asp Val Lys Leu Val Glu Ser
                325                 330                 335

Phe Ile Ser Asp His Lys Gln Arg Gln Gly Asn
                340                 345

<210> SEQ ID NO 15
<211> LENGTH: 4871
<212> TYPE: DNA
<213> ORGANISM: Artificial Sequence
<220> FEATURE:
<223> OTHER INFORMATION: Artificial plasmid pALM173

<400> SEQUENCE: 15
actgccgcac tcaatgttca accagatcta gtgattattt cggggttagc agccgatgcg    60
ggcaacctgg tgaagcaact gcgagaatta ggttacaacg gcattattgt tggggggaac   120
ggcttaaata cttctaatat tttccccgtc tgccaagcaa atgtgatgg ggtgttggtg    180 gcccaagcct acagtgccga gttagataat gagattaacc gcgcgtttcg ggacgcctat   240
tttcaacaaa accaaaaaga gccgccccaa tttagtgccc aggcttttac ggcgatccaa   300 gttttgttg aagccctcag cagcctcgat gaaaaaacgc ccttagaaac tcttgctcta   360
ccggacttgc gacgacaact gcgggacgaa attttgcag gtacctacgt cacgcctttg    420
ggtgaaattt ccttcacaga ggaagggaa attgtccaga aggaattttt tgtggcccaa    480
attgaaatgg atgaatcggg tcaacagggg cgtttcgcct tcattgaaac gaactaaagt   540
caaacctagg cctgtgttta aagggggaa tcagttttgt ctttggaatt tactgactcc    600
```

```
cctctggaca tctccaaacg aattgtgagc gctcacaatt cggaattctt aacaaaaaag    660
caggaataaa attaacaaga tgtaattgac ataagtccca tcaccgttgt ataaatgtgt    720
ggaattgtga gcggataaca atttcacaca ccaactcata aagtcaagta ggagattaat    780
tccatggctc ttgtaccaat gagactgctg ttagaccatg cggcggaaaa tggttatggc    840
attcccgctt tcaacgtcaa caacatggag cagatcattt cgatcatgca ggccgctgat    900
gaaaccgaca gccctgtaat tttgcaagct cccgtggtg cccggagcta cgctggggaa    960
aatttcctgc gccatttagt tttggggcg tcgaaacct atcctcacat tcccattgcc    1020
atgcaccaag accacggcaa tagccccgcc acttgctatt ccgccatccg caacggtttc    1080
accagtgtga tgatggacgg ttccttggaa gctgacgcca gaccccgc tagctttgag     1140 tacaacgtta atgtaaccgc tgaagtagtt aaagtagccc actccgttgg ggccagtgta    1200 gaagggaat tgggttgctt aggttccttg gaaactggtc aaggggaagc tgaagacggc    1260
cacggttttg aagggaagtt agaccactcc caactgttga ccgatcccga agaagcagtg    1320
gaattcgtca acaaaaccca ggtggatgcc ctcgctgtgg cgatcggtac cagccatggt    1380
gcctacaaat ttacccgcaa acccaccggt gaagttttgg ccatcagccg cattgaagaa    1440
attcaccgcc tgctgcccaa cacccacttg gtaatgcacg gttcttcctc cgttccccag    1500
gaatggatcg acatgatcaa cgaattcggt ggtgctatcc ccgaaaccta tggtgtgccc    1560
gtggaagaaa ttcaaaaagg catcaagagt ggtgtacgta aagtaaacat cgacaccgat    1620
aatcgcttag ccatcaccgc cgcttttccgg gaagccgctg ctaaagatcc caagaacttt    1680
gatccccgtc acttcctcaa gccttctatc aaatatatga gcaggtttg tgccgatcgc    1740 tatcaacagt tctggactgc tggcaatgcc tctaaaatca agcaattgac cttggatgac    1800
tacgccgcta aatatgccaa aggtgaatta accgccacct cccgcacctc cgttgctgtg    1860
tagtgaggat ccagggattt aattccatga ccgttagtga gattcatatt cctaactctt    1920
tactagaccg ggattgcacc cccttcac gccacgtact ccaacaactg aatagctttg      1980
gggccgatgc ccaggatttg agtgccatca tgaaccgcat tgccctagcg ggaaaactga    2040
ttgcccgtcg cctgagtcga gctgggttaa tggccgatgt gttgggcttc actggggaaa    2100
ccaacgtcca gggggaatcg gtgaaaaaaa tggacgtatt tgccaatgat gtttttattt    2160
ctgtctttaa gcaaagtggc ttggtttgtc gtctggcttc ggaggagatg gaaaaaccct    2220
actatattcc tgaaaattgc cccattggtc gctatacttt gctgtacgac cccattgatg    2280
gttcctccaa cgtggacatt aacctcaacg tgggttccat ttttgccatt cggcaacagg    2340
aaggggacga tctagacggc agtgcgtcag atttattggc taacggagac aagcaaattg    2400
ctgctggtta tatcctctac ggcccctcca ccatcctggt ttattccctc ggctccggag    2460
tgcatagctt tatcctcgat cccagttttgg gggaatttat tttagcccag gaaaatatcc    2520
gcattcccaa ccacggcccc atttacagca ccaatgaagg taacttttgg caatgggatg    2580
aagccctgag ggattacacc cgttacgtcc atcgccacga aggttacact gcccgttata    2640
gcggtgctct ggtgggggat attaccggga ttttgatgca aggggagtg tttctttatc    2700 ctggtacgga aaaaaatccc gacggcaaat tgcgtttgct ctatgaaact gcgccgctgg    2760
cctttttggt ggaacaggct gggggaaggg ctagtgacgg ccaaaaacgt ttactggact    2820
taattccttc taaattacat cagcgtaccc ccgccattat tggcagcgca gaagatgtga    2880
aattggtgga atctttcatc agcgaccaca acaacggca gggtaattag ggctgctaac    2940
```

```
aaagcccgaa aggaagctga gttggctgct gccaccgctg agcaataact agcataaccc    3000
cttgggccct ctaaacgggt cttgacgggt tttttgtcta gatcaacggc ctcaacctac    3060
tactgggctg cttcctaatg caggagtcgc ataagggaga gcgtcgagat cccggacacc    3120
atcgaatggc gcatttacag ctagctcagt cctaggtaca atgctagccg gaggagggtc    3180
aattcatggt ggtgaatgtg aaaccagtaa cgttatacga tgtcgcagag tatgccggtg    3240
tctcttatca gaccgtttcc cgcgtggtga accaggccag ccacgtttct gcgaaaacgc    3300
gggaaaaagt ggaagcggcg atggcggagc tgaattacat tcccaaccgc gtggcacaac    3360
aactggcggg caaacagtcg ttgctgattg gcgttgccac ctccagtctg gccctgcacg    3420
cgccgtcgca aattgtcgcg gcgattaaat ctcgcgccga tcaactgggt gccagcgtgg    3480
tggtgtcgat ggtagaacga agcggcgtcg aagcctgtaa agcggcggtg cacaatcttc    3540
tcgcgcaacg cgtcagtggg ctgatcatta actatccgct ggatgaccag gatgccattg    3600
ctgtggaagc tgcctgcact aatgttccgg cgttatttct tgatgtctct gaccagacac    3660
ccatcaacag tattatttt tcccatgaag acggtacgcg actgggcgtg gagcatctgg    3720
tcgcattggg tcaccagcaa atcgcgctgt tagcgggccc attaagttct gtctcggcgc    3780
gtctgcgtct ggctggctgg cataaatatc tcactcgcaa tcaaattcag ccgatagcgg    3840
aacgggaagg cgactttagt gccatgtccg gttttcaaca aaccatgcaa atgctgaatg    3900
agggcatcgt tcccactgcg atgctggttg ccaacgatca gatggcgctg gcgcaatgc    3960 gcgccattac cgagtccggg ctgcgcgttg gtgcggatat ctcggtagtg ggatacgacg    4020
ataccgaaga cagctcatgt tatatcccgc cgttaaccac catcaaacag gattttcgcc    4080
tgctggggca aaccagcgtg gaccgcttgc tgcaactctc tcagggccag gcggtgaagg    4140
gcaatcagct gttgcccgtc tcactggtga aagaaaaac caccctggcg cccaatacgc    4200
aaaccgcctc tccccgcgcg ttggccgatt cattaatgca gctggcacga caggtttccc    4260
gactggaaag cgggcagtga gcgcaacgca attaatgtaa gttagctcac tcattaggca    4320
ccgggatctc gaccgatgcc cttgagagcc ttcaacccag tcagctcctt ccggttcgcg    4380
ctcaagttga tcgaatgtat gccccggata tgacctaggg agattcttct aaagcgagca    4440
gggtttgcca agtggcgatc gcctcaggga accataacca actttgttcg aggcggcggg    4500
ggttgagctg ggaacgatcg agatctaggg cgatcgcccg tagggaaagc cgaaaaactc    4560
caagaatttc ctggtcaacg tcggtgggtt gcctttgggc caaatcgtac atactaatcg    4620
ccaggcccgc ataaatctcc gcctggaggg ctgggggga atcctgggtc gttgccgccg    4680
ctaaggcttc ataccaacga tcattggcgg cttcgtaatc tgcattgagg taatggacaa    4740
aacccagggc catcaaaatt tcggggtcgt tgggctgttg ggctagggcc atgtcccaat    4800
tgtcttgcac cgtggcgatc gccgttgctt gggttggcga tggtgggacg gcagccaaag    4860
ttgtttgcca g                                                        4871
```

<210> SEQ ID NO 16
<211> LENGTH: 5323
<212> TYPE: DNA
<213> ORGANISM: Artificial Sequence
<220> FEATURE:
<223> OTHER INFORMATION: Artificial plasmid pALM210

<400> SEQUENCE: 16

```
agcgattggc tatgatctac caaagctggc gattttctg caaaccgaat tagaaccaca      60
atttgatttt ttaaagccga ttaccattgc caacctgaag gaaatagcga tcgcctttat    120
```

-continued

```
ggaggatggc cacgaggctt gtcgggtctc ccattattgt ggatcggtac cggatgagcg    180
ggcgagcttt aatttacgct tgcggcaata tcgccaggcc cagccttggc tgcgaaatca    240
tctcgatcct gcaaggggcg atcgcctgca ccattggtcg gatcaccaac gcaccatttt    300
ctacggcagg cgcaccaatc ccgacaccca gcagcggctt gtgttagtgg cgcacatggc    360
cggggctccg aagaccgttg agattggcaa atggctcgcc ctggatttgg atcgttggca    420
gttggcgatc gccacaccga ctttgaagat caacaccatc tatgacttag cccaaattca    480
cttgcacaat ggcgaaggtt ttctgttatc tgaaattcct ccctaaatga tgtcttttga    540
gcctaaaaac acactttttt gacctaattt aacccattta aaaaacttta tttaataatg    600
accatggccc atcaaaaata cattcttgcg ttagacctcg gtaccacaaa cgaattgtga    660
gcgctcacaa ttcggaattc ttaacaaaaa agcaggaata aaattaacaa gatgtaacag    720
acataagtcc catcaccgtt gtataaatgt gtggaattgt gagcggataa caatttcaca    780
caccaactca taaagtcaag taggagatta attccatggt tagtttagag aagaacgatc    840
acttaatgtt ggcgcgccag ctgccattga atctgttgc cctgatactg cgggaggac     900 gtggtacccg cctgaaggat ttaaccaata agcgagcaaa accggccgta cacttcggcg    960
gtaagttccg cattatcgac tttgcgctgt ctaactgcat caactccggg atccgtcgta   1020
tgggcgtgat cacccagtac cagtcccaca ctctggtgca gcacattcag cgcggctggt   1080
cattcttcaa tgaagaaatg aacgagtttg tcgatctgct gccagcacag cagagaatga   1140
aaggggaaaa ctggtatcgc ggcaccgcag atgcggtcac ccaaaacctc gacattatcc   1200
gccgttataa agcggaatac gtggtgatcc tggcgggcga ccatatctac aagcaagact   1260
actcgcgtat gcttatcgat cacgtcgaaa aaggcgcacg ttgcaccgtt gcttgtatgc   1320
cagtaccgat tgaagaagcc tccgcatttg gcgttatggc ggttgatgag aacgataaaa   1380
ttatcgaatt cgttgaaaaa cctgctaacc cgccgtcaat gccgaacgat ccgagcaaat   1440
ctctggcgag tatgggtatc tacgtctttg acgccgacta tctgtatgaa ctgctggaag   1500
aagacgatcg cgatgagaac tccagccacg actttggcaa agatttgatt cccaagatca   1560
ccgaagccgg tctggcctat gcgcacccgt tcccgctctc ttgcgtacaa tccgacccgg   1620
atgccgagcc gtactggcgc gatgtgggta cgctggaagc ttactggaaa gcgaacctcg   1680
atctggcctc tgtggtgccg gaactggata tgtacgatcg caattggcca attcgcacct   1740
acaatgaatc attaccgcca gcgaaattcg tgcaggatcg ctccggtagc cacgggatga   1800
cccttaactc actggtttcc ggcggttgtg tgatctccgg ttcggtggtg gtgcagtccg   1860
ttctgttctc gcgcgttcgc gtgaattcat tctgcaacat tgattccgcc gtattgttac   1920
cggaagtatg ggtaggtcgc tcgtgccgtc tgcgccgctg cgtcatcgat cgtgcttgtg   1980
ttattccgga aggcatggtg attggtgaaa acgcagagga agatgcacgt cgtttctatc   2040
gttcagaaga aggcatcgtg ctggtaacgc gcgaaatgct acggaagtta gggcataaac   2100
aggagcgata ataacaaagc ccgaaaggaa gctgagttgg ctgctgccac cgctgagcaa   2160
taactagcat aacccccttgg ggcctctaaa cgggtcttga cgggtttttt gtctagatca   2220
acggcctcaa cctactactg ggctgcttcc taatgcagga gtcgcataag ggagagcgtc   2280
gagatcccgg acaccatcga atggcgcatt tacagctagc tcagtcctag gtacaatgct   2340
agccggagga gggtcaattc atggtggtga atgtgaaacc agtaacgtta tacgatgtcg   2400
cagagtatgc cggtgtctct tatcagaccg tttcccgcgt ggtgaaccag gccagccacg   2460
```

```
tttctgcgaa aacgcgggaa aaagtggaag cggcgatggc ggagctgaat tacattccca    2520
accgcgtggc acaacaactg gcgggcaaac agtcgttgct gattggcgtt gccacctcca    2580
gtctggccct gcacgcgccg tcgcaaattg tcgcggcgat taaatctcgc gccgatcaac    2640
tgggtgccag cgtggtggtg tcgatggtag aacgaagcgg cgtcgaagcc tgtaaagcgg    2700
cggtgcacaa tcttctcgcg caacgcgtca gtgggctgat cattaactat ccgctggatg    2760
accaggatgc cattgctgtg gaagctgcct gcactaatgt tccggcgtta tttcttgatg    2820
tctctgacca gacacccatc aacagtatta ttttctccca tgaagacggt acgcgactgg    2880
gcgtggagca tctggtcgca ttgggtcacc agcaaatcgc gctgttagcg ggcccattaa    2940
gttctgtctc ggcgcgtctg cgtctggctg gctggcataa atatctcact cgcaatcaaa    3000
ttcagccgat agcggaacgg gaaggcgact ttagtgccat gtccggtttt caacaaacca    3060
tgcaaatgct gaatgagggc atcgttccca ctgcgatgct ggttgccaac gatcagatgg    3120
cgctgggcgc aatgcgcgcc attaccgagt ccgggctgcg cgttggtgcg gatatctcgg    3180
tagtgggata cgacgatacc gaagacagct catgttatat cccgccgtta accaccatca    3240
aacaggattt tcgcctgctg ggcaaaacca gcgtggaccg cttgctgcaa ctctctcagg    3300
gccaggcggt gaagggcaat cagctgttgc ccgtctcact ggtgaaaaga aaaccaccc    3360 tggcgcccaa tacgcaaacc gcctctcccc gcgcgttggc cgattcatta atgcagctgg    3420
cacgacaggt ttcccgactg gaaagcgggc agtgagcgca acgcaattaa tgtaagttag    3480
ctcactcatt aggcaccggg atctcgaccg atgcccttga gagccttcaa cccagtcagc    3540
tccttccggt tctcgagcgc atgcataaaa actgttgtaa ttcattaagc attctgccga    3600
catggaagcc atcacaaacg gcatgatgaa cctgaatcgc cagcggcatc agcaccttgt    3660
cgccttgcgt ataatatttg cccatggacg cacaccgtgg aaacggatga aggcacgaac    3720
ccagttgaca taagcctgtt cggttcgtaa actgtaatgc aagtagcgta tgcgctcacg    3780
caactggtcc agaaccttga ccgaacgcag cggtggtaac ggcgcagtgg cggttttcat    3840
ggcttgttat gactgttttt ttgtacagtc tatgcctcgg gcatccaagc agcaagcgcg    3900
ttacgccgtg ggtcgatgtt tgatgttatg gagcagcaac gatgttacgc agcagcaacg    3960
atgttacgca gcagggcagt cgccctaaaa caaagttagg tggctcaagt atgggcatca    4020
ttcgcacatg taggctcggc cctgaccaag tcaaatccat gcgggctgct cttgatcttt    4080
tcggtcgtga gttcggagac gtagccacct actcccaaca tcagccggac tccgattacc    4140
tcgggaactt gctccgtagt aagacattca tcgcgcttgc tgccttcgac caagaagcgg    4200
ttgttggcgc tctcgcggct tacgttctgc ccaggtttga gcagccgcgt agtgagatct    4260
atatctatga tctcgcagtc tccggcgagc accggaggca gggcattgcc accgcgctca    4320
tcaatctcct caagcatgag gccaacgcgc ttggtgctta tgtgatctac gtgcaagcag    4380
attacggtga cgatcccgca gtggctctct atacaaagtt gggcatacgg gaagaagtga    4440
tgcactttga tatcgaccca agtaccgcca cctaacaatt cgttcaagcc gagatcggct    4500
tcccggccgc ggagttgttc ggtaaattgt cacaacgccg ccaggtggca cttttcgggg    4560
aaatgtgcgc gcccgcgttc ctgctggcgc tgggcctgtt tctggcgctg acttcccgc    4620 tgttccgtca gcagcttttc gcccacggcc ttgatgatcg cggcggcctt ggcctgcata    4680
tcccgattca acggccccag ggcgtccaga acgggcttca ggcgctcccg aaggtggatc    4740
cccccctctt gcctacagca tctccccag gggagaattc ttcctgtttc aactccctct    4800
aacgtaaacc cattgaattt aaaaaagact ttatgactgc tttactgctc catgaccaac    4860
```

```
attattccct tgatcatgaa gcctttctct caaccctcag caacacagaa aatttactca    4920
ttattcaaga tctagatggc gtttgcatgg ggttagtcaa agacccctta acccgcaaaa    4980
ttgatcctga ctatatccgc gccacacgca agtttagaga ccacttcttt gtcctcacca    5040
acggtgaaca tgaaggcaga agggagtaa  atcgcatcgt tgaacgggca tttcgcaatg    5100
ttgaagccaa agaggaaaca agctatttac ctggtttagc agcaggggt  gtgcaatggc    5160 agacagataa tggccaaatt tcccatcccg gtgttagcca agcagaactc gatttccttg    5220
ccacagtgcc agatttaatt ggtcaaagtt taggacaatt ttttactaaa tatgttgata    5280
tttttcccgc tgagcttcaa cctgagctga tccatgcttc tgt                      5323

<210> SEQ ID NO 17
<211> LENGTH: 5323
<212> TYPE: DNA
<213> ORGANISM: Artificial Sequence
<220> FEATURE:
<223> OTHER INFORMATION: Artificial plasmid pALM211

<400> SEQUENCE: 17
agcgattggc tatgatctac caaagctggc gattttctg  caaaccgaat tagaaccaca      60
atttgatttt ttaaagccga ttaccattgc caacctgaag gaaatagcga tcgcctttat     120
ggaggatggc cacgaggctt gtcgggtctc ccattattgt ggatcggtac cggatgagcg     180
ggcgagcttt aatttacgct tgcggcaata tcgccaggcc cagccttggc tgcgaaatca     240
tctcgatcct gcaaggggcg atcgcctgca ccattggtcg gatcaccaac gcaccatttt     300
ctacggcagg cgcaccaatc ccgacaccca gcagcggctt gtgttagtgg cgcacatggc     360
cggggctccg aagaccgttg agattggcaa atggctcgcc ctggatttgg atcgttggca     420
gttggcgatc gccacaccga cttttgaagat caacaccatc tatgacttag cccaaattca    480
cttgcacaat ggcgaaggtt ttctgttatc tgaaattcct ccctaaatga tgtcttttga    540
gcctaaaaac acactttttt gacctaattt aacccatttt aaaaacttta tttaataatg    600
accatggccc atcaaaaata cattcttgcg ttagacctcg gtaccacaaa cgaattgtga    660
gcgctcacaa ttcggaattc ttaacaaaaa agcaggaata aaattaacaa gatgtaacag    720
acataagtcc catcaccgtt gtataaatgt gtggaattgt gagcggataa caatttcaca    780
caccaactca taaagtcaag taggagatta attccatggt tagtttagag aagaacgatc    840
acttaatgtt ggcgcgccag ctgccattga aatctgttgc cctgatactg gcgggaggac    900
gtggtacccg cctgaaggat ttaaccaata agcgagcaaa accggccgta cacttcggcg    960
gtaagttccg cattatcgac tttgcgctgt ctaactgcat caactccggg atccgtcgta   1020
tgggcgtgat caccagtac  cagtcccaca ctctggtgca gcacattcag cgcggctggt   1080
cattcttcaa tgaagaaatg aacgagtttg tcgatctgct gccagcacag cagagaatga   1140
aaggggaaaa ctggtatcgc ggcaccgcag atgcggtcac ccaaaacctc gacattatcc   1200
gccgttataa agcggaatac gtggtgatcc tggcgggcga ccatatctac aagcaagact   1260
actcgcgtat gcttatcgat cacgtcgaaa aaggcgcacg ttgcaccgtt gcttgtatgc   1320
cagtaccgat tgaagaagcc tccgcatttg gcgttatggc ggttgatgag aacgataaaa   1380
ttatcgaatt tgttgaaaaa cctgctaacc cgccgtcaat gccgaacgat ccgagcaaat   1440
ctctggcgag tatgggtatc tacgtctttg acgccgacta tctgtatgaa ctgctggaag   1500
aagacgatcg cgatgagaac tccagccacg actttggcaa agatttgatt cccaagatca   1560
```

```
ccgaagccgg tctggcctat gcgcacccgt tcccgctctc ttgcgtacaa tccgacccgg      1620
atgccgagcc gtactggcgc gatgtgggta cgctggaagc ttactggaaa gcgaacctcg      1680
atctggcctc tgtggtgccg gaactggata tgtacgatcg caattggcca attcgcacct      1740
acaatgaatc attaccgcca gcgaaattcg tgcaggatcg ctccggtagc cacgggatga      1800
cccttaactc actggtttcc gacggttgtg tgatctccgg ttcggtggtg gtgcagtccg      1860
ttctgttctc gcgcgttcgc gtgaactcat tctgcaacat tgattccgcc gtattgttac      1920
cggaagtatg ggtaggtcgc tcgtgccgtc tgcgccgctg cgtcatcgat cgtgcttgtg      1980
ttattccgga aggcatggtg attggtgaaa cgcagagga agatgcacgt cgtttctatc      2040
gttcagaaga aggcatcgtg ctggtaacgc gcgaaatgct acggaagtta gggcataaac      2100
aggagcgata ataacaaagc ccgaaaggaa gctgagttgg ctgctgccac cgctgagcaa      2160
taactagcat aaccccttgg ggcctctaaa cgggtcttga cgggtttttt gtctagatca      2220
acggcctcaa cctactactg ggctgcttcc taatgcagga gtcgcataag ggagagcgtc      2280
gagatcccgg acaccatcga atggcgcatt tacagctagc tcagtcctag gtacaatgct      2340
agccggagga gggtcaattc atggtggtga atgtgaaacc agtaacgtta tacgatgtcg      2400
cagagtatgc cggtgtctct tatcagaccg tttcccgcgt ggtgaaccag gccagccacg      2460
tttctgcgaa aacgcgggaa aaagtggaag cggcgatggc ggagctgaat tacattccca      2520
accgcgtggc acaacaactg gcgggcaaac agtcgttgct gattggcgtt gccacctcca      2580
gtctggccct gcacgcgccg tcgcaaattg tcgcggcgat taaatctcgc gccgatcaac      2640
tgggtgccag cgtggtggtg tcgatggtag aacgaagcgg cgtcgaagcc tgtaaagcgg      2700
cggtgcacaa tcttctcgcg caacgcgtca gtgggctgat cattaactat ccgctggatg      2760
accaggatgc cattgctgtg gaagctgcct gcactaatgt tccggcgtta tttcttgatg      2820
tctctgacca gacacccatc aacagtatta ttttctccca tgaagacggt acgcgactgg      2880
gcgtggagca tctggtcgca ttgggtcacc agcaaatcgc gctgttagcg ggcccattaa      2940
gttctgtctc ggcgcgtctg cgtctggctg gctggcataa atatctcact cgcaatcaaa      3000
ttcagccgat agcggaacgg gaaggcgact ttagtgccat gtccggtttt caacaaacca      3060
tgcaaatgct gaatgagggc atcgttccca ctgcgatgct ggttgccaac gatcagatgg      3120
cgctgggcgc aatgcgcgcc attaccgagt ccgggctgcg cgttggtgcg gatatctcgg      3180
tagtgggata cgacgatacc gaagacagct catgttatat cccgccgtta accaccatca      3240
aacaggattt tcgcctgctg gggcaaacca gcgtggaccg cttgctgcaa ctctctcagg      3300
gccaggcggt gaagggcaat cagctgttgc ccgtctcact ggtgaaaaga aaaccaccc      3360 tggcgcccaa tacgcaaacc gcctctcccc gcgcgttggc cgattcatta atgcagctgg      3420
cacgacaggt ttcccgactg aaagcgggc agtgagcgca acgcaattaa tgtaagttag      3480
ctcactcatt aggcaccggg atctcgaccg atgcccttga gagccttcaa cccagtcagc      3540
tccttccggt tctcgagcgc atgcataaaa actgttgtaa ttcattaagc attctgccga      3600
catggaagcc atcacaaacg gcatgatgaa cctgaatcgc cagcggcatc agcaccttgt      3660
cgccttgcgt ataatatttg cccatggacg cacaccgtgg aaacggatga aggcacgaac      3720
ccagttgaca taagcctgtt cggttcgtaa actgtaatgc aagtagcgta tgcgctcacg      3780
caactggtcc agaaccttga ccgaacgcag cggtggtaac ggcgcagtgg cggttttcat      3840
ggcttgttat gactgttttt ttgtacagtc tatgcctcgg gcatccaagc agcaagcgcg      3900
ttacgccgtg ggtcgatgtt tgatgttatg gagcagcaac gatgttacgc agcagcaacg      3960
```

```
atgttacgca gcagggcagt cgccctaaaa caaagttagg tggctcaagt atgggcatca    4020
ttcgcacatg taggctcggc cctgaccaag tcaaatccat gcgggctgct cttgatcttt    4080
tcggtcgtga gttcggagac gtagccacct actcccaaca tcagccggac tccgattacc    4140
tcgggaactt gctccgtagt aagacattca tcgcgcttgc tgccttcgac caagaagcgg    4200
ttgttggcgc tctcgcggct tacgttctgc ccaggtttga gcagccgcgt agtgagatct    4260
atatctatga tctcgcagtc tccggcgagc accggaggca gggcattgcc accgcgctca    4320
tcaatctcct caagcatgag gccaacgcgc ttggtgctta tgtgatctac gtgcaagcag    4380
attacggtga cgatcccgca gtggctctct atacaaagtt gggcatacgg aagaagtga    4440 tgcactttga tatcgaccca agtaccgcca cctaacaatt cgttcaagcc gagatcggct    4500
tcccggccgc ggagttgttc ggtaaattgt cacaacgccg ccaggtggca cttttcgggg    4560
aaatgtgcgc gcccgcgttc ctgctggcgc tgggcctgtt tctggcgctg gacttcccgc    4620
tgttccgtca gcagcttttc gcccacggcc ttgatgatcg cggcggcctt ggcctgcata    4680
tcccgattca acggcccag ggcgtccaga acgggcttca ggcgctcccg aaggtggatc    4740
cccccctctt gcctacagca tctcccccag gggagaattc ttcctgtttc aactccctct    4800
aacgtaaacc cattgaattt aaaaaagact ttatgactgc tttactgctc catgaccaac    4860
attattccct tgatcatgaa gcctttctct caaccctcag caacacagaa aatttactca    4920
ttattcaaga tctagatggc gtttgcatgg ggttagtcaa agaccccta acccgcaaaa    4980 ttgatcctga ctatatccgc gccacacgca agtttagaga ccacttcttt gtcctcacca    5040
acggtgaaca tgaaggcaga aggggagtaa atcgcatcgt tgaacgggca tttcgcaatg    5100
ttgaagccaa agaggaaaca agctatttac ctggtttagc agcaggggt gtgcaatggc    5160 agacagataa tggccaaatt tcccatcccg gtgttagcca agcagaactc gatttccttg    5220
ccacagtgcc agatttaatt ggtcaaagtt taggacaatt ttttactaaa tatgttgata    5280
tttttcccgc tgagcttcaa cctgagctga tccatgcttc tgt                      5323
```